(12) United States Patent
Hill et al.

(10) Patent No.: US 7,074,220 B2
(45) Date of Patent: Jul. 11, 2006

(54) METHODS AND SYSTEMS FOR VEIN HARVESTING AND FISTULA CREATION

(75) Inventors: Bradley Hill, Woodside, CA (US); Neil Holmgren, Alameda, CA (US); Bruce Modesitt, San Carlos, CA (US)

(73) Assignee: Thomas J. Fogarty, Portola Valley, CA (US)

( * ) Notice: Subject to any disclaimer, the term of this patent is extended or adjusted under 35 U.S.C. 154(b) by 51 days.

(21) Appl. No.: 10/366,535

(22) Filed: Feb. 12, 2003

(65) Prior Publication Data

US 2003/0225426 A1 Dec. 4, 2003

Related U.S. Application Data

(63) Continuation-in-part of application No. 10/116,730, filed on Apr. 3, 2002, now Pat. No. 6,551,314.

(51) Int. Cl.
*A61B 18/18* (2006.01)
(52) U.S. Cl. .......................... 606/45; 606/190
(58) Field of Classification Search ............ 606/32–34, 606/45–52, 190, 194
See application file for complete search history.

(56) References Cited

U.S. PATENT DOCUMENTS

| | | |
|---|---|---|
| 2,779,334 A | 1/1957 | Sandborn |
| 3,045,676 A | 7/1962 | Slaten |
| 3,185,155 A | 5/1965 | Slaten et al. |
| 3,568,677 A | 3/1971 | Nolan et al. |
| 3,788,325 A | 1/1974 | Jacobsen |
| 4,528,982 A | 7/1985 | Wellenstam |
| 4,793,346 A | 12/1988 | Mindich |
| 5,593,418 A | 1/1997 | Mollenauer |
| 5,658,282 A * | 8/1997 | Daw et al. ................. 606/49 |
| 5,667,480 A | 9/1997 | Knight et al. |
| 5,695,514 A | 12/1997 | Chin |
| 5,797,947 A | 8/1998 | Mollenauer |
| 5,817,013 A | 10/1998 | Ginn et al. |
| 5,843,104 A | 12/1998 | Samuels |
| 5,853,417 A | 12/1998 | Fogarty et al. |

(Continued)

FOREIGN PATENT DOCUMENTS

WO WO 00/45691 8/2000

OTHER PUBLICATIONS

Illig et al., Transposed saphenous vein arteriovenous fistula revisited: new technology for an old idea; Division of Vascular Surgery, University of Rochester Medical Center, Rochester, NY, PMID: 12044427.

*Primary Examiner*—Michael Peffley
*Assistant Examiner*—Aaron Roane
(74) *Attorney, Agent, or Firm*—Townsend and Townsend and Crew LLP

(57) ABSTRACT

Veins are removed using a pull catheter introduced over a guidewire which extends between first and second percutaneous access points. Optionally, a side branch management tool including an excision device and/or a viewing scope can be advanced over the same guidewire in the direction opposite to that of the pull catheter. In that way, as the pull catheter inverts the vein being removed, side branches can be selectively viewed and/or severed using the side branch management tool. Arteriovenous fistulas are formed by inverting a length of a vein, mobilizing the inverted length relocating the mobilized end of the vein, and connecting the mobilized end to an artery.

13 Claims, 24 Drawing Sheets

U.S. PATENT DOCUMENTS

| | | |
|---|---|---|
| RE36,043 E | 1/1999 | Knighton |
| 5,899,913 A | 5/1999 | Fogarty et al. |
| 5,902,315 A | 5/1999 | DuBois |
| 5,902,316 A | 5/1999 | Mollenauer |
| 5,922,004 A | 7/1999 | DuBois |
| 5,928,138 A | 7/1999 | Knight et al. |
| 5,944,734 A | 8/1999 | Hermann et al. |
| 5,968,066 A | 10/1999 | Fogarty et al. |
| 5,993,412 A | 11/1999 | Deily et al. |
| 6,013,073 A | 1/2000 | Choukroun |
| 6,022,313 A | 2/2000 | Ginn et al. |
| 6,030,396 A * | 2/2000 | Samuels ................. 606/159 |
| 6,068,639 A | 5/2000 | Fogarty et al. |
| 6,077,289 A | 6/2000 | Mollenauer |
| 6,165,172 A | 12/2000 | Farley et al. |
| 6,196,968 B1 | 3/2001 | Rydin et al. |
| 6,551,314 B1 * | 4/2003 | Hill et al. ................. 606/45 |

* cited by examiner

METHODS AND SYSTEMS FOR VEIN HARVESTING AND FISTULA CREATION

CROSS-REFERENCES TO RELATED APPLICATIONS

This application is a continuation-in-part of application Ser. No. 10/116,730, filed Apr. 3, 2002 now U.S. Pat. No. 6,551,314, the full disclosure of which is incorporated herein by reference.

BACKGROUND OF THE INVENTION

1. Field of the Invention

The present invention relates generally to medical apparatus and methods. More particularly, the present invention relates to methods and systems for vascular surgery, including intraluminal vein harvesting and fistula creation.

Cardiac and peripheral vascular bypass surgery commonly employs veins harvested from the patient undergoing surgery, usually obtained by autologous vein harvesting procedures. Vein harvesting commonly relies on making a long skin incision to expose the length of vein which is to be excised and removed. Such exposure of the vein allows for dissection and division of the veins which branch from the portion of vein being removed. The greater saphenous vein in the leg is most commonly used, followed by the lesser saphenous vein in the leg and the basilic and cephalic veins in the arm.

Such long incisions made for vein harvesting are highly traumatic and problematic for a number of reasons. First, patients requiring bypass surgery often suffer from other diseases, such as diabetes, obesity, malnutrition, which may impede healing and increase the risk of infection of the skin incisions. Additionally, the cosmetic scarring which results from the long incisions is of concern to many patients.

To partly overcome these drawbacks, systems for the endoscopic harvesting of veins have been developed. Such systems, presently available from suppliers such as Ethicon and General Surgical Innovations, rely on introduction of endoscopic apparatus through an incision at one end of the vein segment to be removed. The apparatus includes a viewing scope, a mechanism for dissecting the vein from the surrounding tissue bed, and additional mechanisms for dissecting the vein from side branches to facilitate removal. Other systems, such as that available from Guidant Corporation, use gas insufflation to create a working space around the vein and rely on percutaneously introduced instruments for excising the vein. In all cases, the systems are expensive, cumbersome to use, and still traumatic to the patient.

Arteriovenous fistulas (AVFs) are another difficult vascular surgery which require long incisions and extensive surgical dissections. In particular, autologous AVF procedures in the upper arm between the brachial artery and the basilic vein can be problematic. The present techniques generally require that a patient be placed under general anesthetic for vein transposition and anastomosis.

For these reasons, it would be desirable to provide improved vein harvesting apparatus and methods for performing vascular surgeries, including vein harvesting and AVF procedures. Such improved surgeries would preferably be minimally traumatic to the patient, do not require long skin penetrations or incisions at points between the two ends of the vein segment being removed, permit selective excision of the venous side branches and optional sealing of the side branches, and provide a vein segment which is maintained relatively intact, allows for valve removal and can be used for bypass grafting AVF formation, or other purposes with minimal additional preparation. It would be further desirable if the systems and methods were also useful for vein stripping and removal for treatment of varicose veins and other conditions. The system and methods should optionally permit endoscopic visualization of the vein while it is being removed and remove relatively long vein segments with a single device deployment. At least some of these objectives will be met by the inventions described hereinafter.

2. Description of the Background Art

Intraluminal vein removal and modification devices are described in U.S. Pat. Nos. 6,165,172; 6,030,396; 6,013,073; 5,843,104; 4,528,982; 3,788,325; 3,568,677; 3,185,155; 3,045,676; 2,779,334; and PCT Publication WO 00/45691. Endoscopic and extraluminal vein removal devices are described in U.S. Pat. Nos. 6,022,313; 5,817,013; 4,793,346; and Re. 36,053. Patents relating to vein harvesting assigned to General Surgical Innovations include U.S. Pat. Nos. 6,196,968; 6,077,289; 6,068,639; 5,993,412; 5,968,066; 5,944,734; 5,899,913; and 5,853,417. Patents relating to vein harvesting assigned to Ethicon include U.S. Pat. Nos. 6,193,653; 5,928,138; 5,922,004; 5,902,315; and 5,667,480. Use of an endoscopicedly harvested saphenous vein to transposition and anastomosis to the femoral artery is suggested in Illig et al. DMID: 12044427.

BRIEF SUMMARY OF THE INVENTION

The present invention provides improved methods, systems, and kits for removing veins from their surrounding tissue beds. While the methods will find their greatest use in the harvesting of veins for subsequent implantation in bypass and other procedures, they will also find use for removing varicose veins and diseased veins for cosmetic and other purposes. When used for vein harvesting, the target veins will most often be the greater saphenous vein or the lesser saphenous vein in the leg, and the basilic and cephalic veins in the arm.

The present invention is advantageous in a number of respects. It does not require a long incision along the length of the vein segment to be removed. Instead, it is less invasive and may be performed via surgical cut downs at each end of the vein segment to be removed. Additionally, the present invention allows for selective severing of venous side branches from the vein segment being removed during the removal process. In one embodiment of the present invention, such selective severing (and optionally subsequent sealing) of the side branches may be performed under direct endoscopic visualization. In another embodiment, such selective severing is achieved in a blind fashion, greatly simplifying the protocols. Use of the methods and apparatus of the present invention has been found to produce very long and high quality vein segments suitable for coronary artery and other bypass and implantation procedures. In some embodiments, the apparatus of the present invention facilitates manipulation of the long vein segments after they have been removed, in particular allowing trimming of the valves and other preparation steps to be performed while the vein remains over a long distal portion of the vein removal catheter.

In a first aspect, methods according to the present invention for vein removal comprise exposing first and second spaced-apart locations along a vein, typically by surgically exposing the locations, commonly referred to as a surgical cut down. The veins are then transected at each of the locations so that a segment of the vein is isolated and ready for removal from the surrounding tissue bed. The remaining portions of the vein, i.e., those which are not to be removed, may have their free ends tied off or otherwise sealed.

After exposing and transecting the ends of the venous segment to be removed, a guidewire is passed through a lumen between the first and second locations. The length of the guidewire is sufficient to permit introduction of intraluminal devices over at least one end, and preferably over both ends, of the guidewire to perform the methods described herein. In particular, a pull catheter will be introduced over the guidewire from the first location until a distal end of the pull catheter reaches the second location. Usually, the first location will be that which is closest to the patient's heart and which therefore has a larger diameter.

Alternatively, the pull catheter may have a fixed rail at its distal end or the pull catheter may be provided with a rail immobilization mechanism for selectively holding a movable rail with the distal end of the movable rail exposed distally out the pull catheter. In either case, the pull catheter may be introduced to and through the target vein without the prior positioning of a movable rail. With a fixed rail, the rail would be designed to be long enough to allow introduction of a side branch management catheter (as described below) excision or other catheter over a movable rail in a direction opposite to that of the pull catheter. An advantage of using a pull catheter and a fixed rail is that there is no need to separately manipulate a long guidewire, which when both a pull catheter and an side branch management tool are to be introduced, may have a length which is more than three times that of the individual catheters. A similar advantage is found with the use of the immobilized rail, where the rail could have a length only slightly longer than that of the pull catheter. The immobilized guidewire, however, could be released after the pull catheter is extended distally so that it could remain in place as the pull catheter is withdrawn from the vessel. An advantage of both these alternative rail designs, is that introduction of a side branch management or other catheter from the remote tissue penetration, as described below, will be more easier. In addition, the fixed rail embodiment provides support for the inverted vein after removal and can help in re-inverting the vein and other vein preparation steps.

After the pull catheter has been introduced to the desired location, the free end of the vein which has been transected near the second location is attached to the distal catheter end, typically by suturing, clipping, tying, or otherwise circumferentially securing the venous end to the distal end of the pull catheter. The pull catheter is then pulled in a direction back from the second location toward the first location so that the end of the "free" venous segment to be removed is inverted. In particular, the free end is pulled inwardly and to the lumen of the venous segment with a continually retracting inversion fold line being exposed as the vein is pulled from the surrounding tissue bed.

As the venous segment is inverted and pulled from the surrounding tissue bed, the venous wall will be pulled from the side branches which extend radially outwardly into the surrounding tissue bed. In some instances, the wall of the venous segment can simply be pulled or evulsed from the attached end of the side branch. For larger side branches, however, it may be desirable to divide and optionally occlude the side branches from the wall of the venous segment prior to removal of the vein. According to the present invention, this can be accomplished by introducing a side branch management tool, preferably over the guidewire, through the second location and advancing a distal end of the side branch management tool so that it follows an inversion line of the venous segment as it is being inverted. The side branch management tool will usually include at least a cutting tool and may optionally include a sealing tool and/or viewing optics. The cutting tool can be a deployable or fixed blade, an electrosurgical cutting tool, a shearing blade, or the like. The occlusion device could be an electrocautery device, a clip applier, a hemostatic or glue applicator, or the like. The optional optical viewing system will normally comprise an optical fiber system, but could comprise a CCD or other electronic monitor directly on the tool.

Severing of the side branches can be achieved in a number of ways, including both blind and under visualization. Removal of the side branches under visualization can be accomplished, for example, using a catheter having a viewing scope positioned in or alongside the side branch management tool to visualize the inversion folding edge, referred to herein as the inversion line, as the venous segment is inverted. When side branches which need to be severed are observed, a separate or integral cutting blade or other tool can be advanced from the side branch management tool and used to selectively cut the side branch near its attachment point to the venous segment. Blind side branch management tools may comprise simple tubular cutting blades or tubular cutting blades having castellated or serpentine cutting edges. Alternatively, blind tools may comprise a blunt or acorn tip which may be advanced so that it embeds into the inverted venous wall as it is being pulled. Fixed or actuable blade(s) on the tool may then be used to cut the side branches when the user determines that a side branch is impeding the vein removal. Usually, the catheter tip will be rotated so that the blade circumscribes a line positioned just behind the inversion line, thus selectively isolating, tensioning and severing the side branches which are attached at that point. A variety of other cutting mechanisms and protocols could also be used, such as a gripping or clamping tool that pulls vessel out by it's root.

A particular advantage of the present invention is that the visualization and optional cutting of the side branches is accomplished using a side branch management tool introduced in a direction opposite to that of the pull catheter. In contrast to the endoscopic devices of the prior art which combine vessel dissection and side branch excision functions, the separate pull catheter and side branch management tool of the present invention can have relatively low profiles greatly reducing the trauma to the patient which results from advancing the catheters subcutaneously through the tissue bed. Moreover, as the vein is inverted, the side branch management tool can utilize the space left by the removed vein in the tissue bed so that additional dissection is minimized.

Optionally, after the side branches are cut, the side branch management tool can be used to seal portions of the side branch which remains in the tissue bed. For example, the cutting blade which is used to sever the side branches may be connected to an electrocautery power supply (RF or DC current) in order to cauterize the side branches. Alternatively, the side branches could be clipped or stapled, or as a third alternative, the side branches could be sealed using a tissue sealant, such as polyacrylate or a thrombin-based hemostatic agent.

In a second aspect of the present invention, systems for the removal of veins, either for harvesting or varicose vein removal, comprise a pull catheter, a side branch management tool, and usually a separate (immovable) guidewire. The guidewire will be capable of extending from a proximal location to a spaced-apart distal location along a vein. The guidewire will typically have a length in the range from 180 cm to 260 cm and a diameter in the range from 0.2 mm to 0.9 mm (usually 0.035").

The pull catheter will comprise a catheter body having at least one lumen therethrough adapted to permit introduction over the guidewire. Typically, the pull catheter will have an over-the-wire design where the guidewire lumen extends the entire length of the catheter body. Alternatively, the pull catheter could have a shortened guidewire lumen extending over only a portion of the distal end, typically from 5 cm to 25 cm, usually from 5 cm to 15 cm. As a still further alternative, the pull catheter could have a fixed rail at its distal end, typically having a length in the range from 80 cm to 100 cm, usually from 80 cm to 100 cm. When used with movable guidewires, the pull catheter can optionally have a mechanism for capturing the guidewire, such as a clamp, so that a distal portion of the movable guidewire can be extended distally of the distal end of the pull catheter and then immobilized in place. In this way, the pull catheter can be initially introduced through the lumen of the target lumen in a manner analogous to the use of a catheter having a fixed guidewire. After advancing the pull catheter to the remote end of the target lumen, the guidewire can be grasped by the user and released from the catheter so that the catheter may be freely advanced and retracted over the now-movable guidewire. The pull catheter can have at least a second lumen to permit the infusion of saline or other solutions, although combined guidewire and infusion lumens may also find use. As a still further option, the pull catheter may be provided with a balloon near its distal end, where the balloon can be inflated to help initiate inversion of the vein.

Provision will be made at or near the distal end of the pull catheter to permit attachment of a dissected end of the venous segment to be removed. Most simply, the surgeon could use a clip or directly suture the vein through a distal region of the pull catheter. No particular modification of the pull catheter is required. More usually, however, the pull catheter will have a transverse aperture therethrough to permit suture or other type of clipping device to be passed through the catheter and secured over the venous segment. Alternatively, a circumferential channel or trough may be formed in the catheter body to again facilitate suturing or other attachment of the venous wall to the catheter. Of course, the vein could be attached to the pull catheter using clips, staples, metal ties, C-clamps, or in a variety of other ways. In all cases, however, it will be preferable that the free end of the venous segment be attached substantially uniformly about its circumference so that force is transmitted evenly to the vein as it is pulled and inverted from the tissue bed.

The side branch management tool will also comprise a rigid body or catheter having a guidewire lumen or other means for being introduced over a guidewire. Again, the side branch management tool may have an over-the-wire design where a guidewire lumen extends the entire length of the catheter body. Alternatively, the length of the guidewire lumen can be shortened, generally to the ranges set forth above with regard to the pull catheter. The side branch management tool will typically also have some provision for dissecting or cutting the venous side branches from the venous segment which is being withdrawn.

Usually, the side branch management tool will include a fixed or retractable blade attached near a distal end of the side branch management tool. By rotating the catheter, or at least a portion thereof that has the blade, the blade will travel circumferentially around a path which can be aligned with the expected position of the side branches. Alternatively, the blade can have a generally tubular configuration so that it can cut along the entire circumferential surface of the tissue bed as it is being exposed by the venous segment being inverted. In all cases the blade can optionally be connected to an electrosurgical power supply so that the cutting may be enhanced by the application of DC or radiofrequency energy. In such cases, the power supply could also provide radiofrequency energy intended to cauterize the cut surfaces.

The side branch management tool may optionally be provided with a viewing scope to permit visualization of the side branches and to permit more careful positioning of the blade or associated cutting mechanism in order to sever the side branches. Usually, the side branch management tool will have a lumen or other channel for introducing a working tool for cutting the side branch under endoscopic visualization. Numerous blades, scissors, electrosurgical tools, and the like, could be introduced through the side branch management tool and used under endoscopic visualization to selectively cut the side branches. Alternatively, the cutting mechanism may be formed as an integral component of the catheter.

In a specific embodiment, the side branch management tool may have a distal tip that includes a feature, such as a notch or raised edge, to catch and tension a side branch prior to dissection. Such a feature allows the surgeon to feel when the tool has encountered a side branch and further allows the surgeon to then dissect the side branch by firmly engaging the feature against the side branch and rotating, translating, or otherwise manipulating the tool to dissect the side branch. If the side branch is sufficiently small (less than 2 mm in diameter) the surgeon may evulse the branch using forward traction on the side branch management tool. Usually, the tool will also be provided with a cutting blade or other cutting feature which allows the user to first capture and tension the side branch, optionally clip and then selectively actuate the cutting blade to dissect the side branch. Optionally, the side branch management tool will include visualization which permits the surgeon to view the side branch after it has been captured and to observe the side branch as it is being dissected by the cutting blade.

The sizes of both the pull catheter and the side branch management tool may vary depending on the particular venous segment which is to be withdrawn. For the greater and lesser saphenous veins and the basilic and cephalic veins, the catheter bodies will typically have a length in the range from 40 cm to 80 cm and a body diameter in the range from 4 mm to 12 mm.

Kits according to the present invention for vein removal will also comprise a guidewire, a pull catheter, and an side branch management tool. In addition to these components, which preferably will be as described above with respect to the systems, the kits will also include instructions for use setting forth a method according to the present invention for vein removal. The methods may be any of the methods described herein above. Typically, the kits will further include packaging for holding the guidewire, pull catheter, and side branch management tool, preferably all in a sterile condition. Suitable packages include pouches, tubes, boxes, trays, and the like. The instructions for use will typically be printed on a sheet of paper, usually in the form of a product insert. Alternatively, the instructions for use may be printed directly on the packaging. In other cases, the instructions for use may be made available electronically, e.g., on CD-ROMs, sold as a part of the kit, or made available over the Internet. In all cases, the instructions for use will inform the user on how to use the physical components of the kit to perform the methods in an acceptable manner.

The methods and tools of the present invention may also be adapted for creating arteriovenous fistulas (AVFs), i.e., fistulas between a vein and an artery, for providing hemodialysis access or other purposes. The methods rely on inverting a length of vein from a distal location to an exposure point. The vein is divided at the distal location, but unlike the vein harvesting procedures described above, is not divided elsewhere along its length. Thus, the proximal end of the vein remains connected to the venous vasculature. After exposure through the exposure point, the vein can be prepared for attachment to a target artery. The free distal end of the vein is then drawn to the arterial attachment point, typically by tunneling from the desired arterial attachment point to the exposure point. The vein is then anastomosed to the target artery in the conventional manner.

Usually, the vein is inverted by first exposing and transecting the vein at the distal location. A guidewire is then introduced through a lumen of the vein to a point beyond the exposure point, typically being at least as far beyond the exposure point as the length of vein to be exposed and transposed. A push catheter is attached to the transected distal end of the vein, and the vein is inverted by pushing the push catheter back through the venous lumen until an inversion line of the vein reaches the exposure point. The vein is then re-everted externally by drawing the push catheter and guidewire out through the exposure point. The push catheter is then withdrawn over the guidewire to re-evert and externally mobilize the length of vein. In the exemplary embodiments, the vein is the basilic vein, the artery is the brachial artery, the distal location is near the elbow, and the exposure point is the deltopectoral groove.

According to the present invention, kits for arteriovenous fistula formation comprise a push catheter and a tunneling tool. The kits will further comprise instructions for use setting forth the fistula formation methods just described. Typically, the kits will further include packaging for holding the push catheter and tunneling tool, preferably in sterile conditions. Suitable packages include poaches, tubes, boxes, trays, and the like. The instructions for use will typically be printed on a sheet of paper, usually in the form of a product insert. Alternatively, the instructions for use may be printed directly on the packaging. In other cases, the instructions for use may be made available electronically, e.g. on CD-ROMs sold as part of the kit or made available over the Internet. In all cases, the instructions for use will inform the user how to use the physical components of the kit to create the arteriovenous fistula in an acceptable manner.

DESCRIPTION OF SPECIFIC EMBODIMENTS

Figure 1:
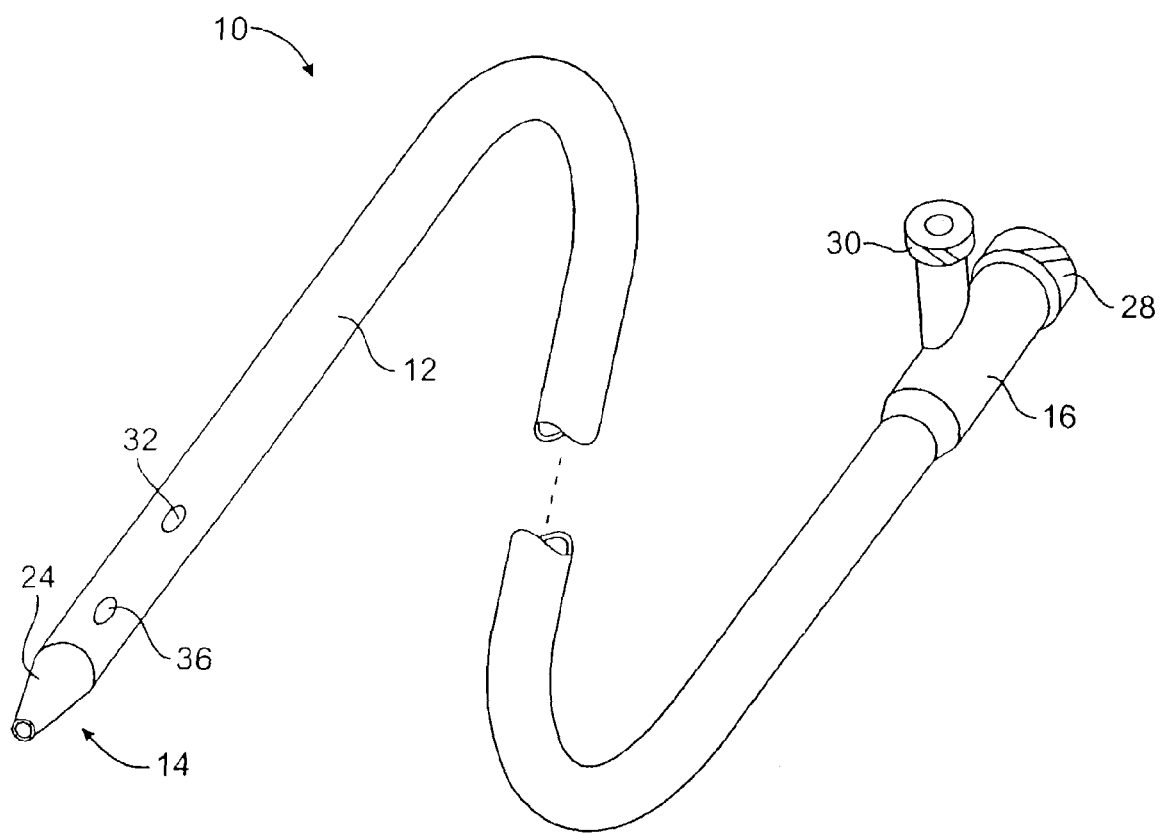
FIG. 1 is a perspective view of a first embodiment of a pull catheter constructed in accordance with the principles of the present invention.

Referring to FIG. 1, a first embodiment of a pull catheter 10 constructed in accordance with the principles of the present invention comprises a catheter body 12 having a distal end 14 and a proximal hub 16. The catheter body 12 will preferably have the dimensions set forth above and may be composed of a single extrusion from a variety of conventional catheter materials such as natural or synthetic polymers, typically polyethylenes, polyvinylchlorides, polyurethanes, polyesters, polytetrafluorethylenes (PTFE's), nylon, silicone rubbers, and the like. Optionally, the catheter body will be reinforced with axial wires, braided layers, helical coils, or the like. The purpose of such enforcement will be to enhance the tensile strength of the catheter which is used primarily for pulling on the venous segment which is being removed.

Figure 2:
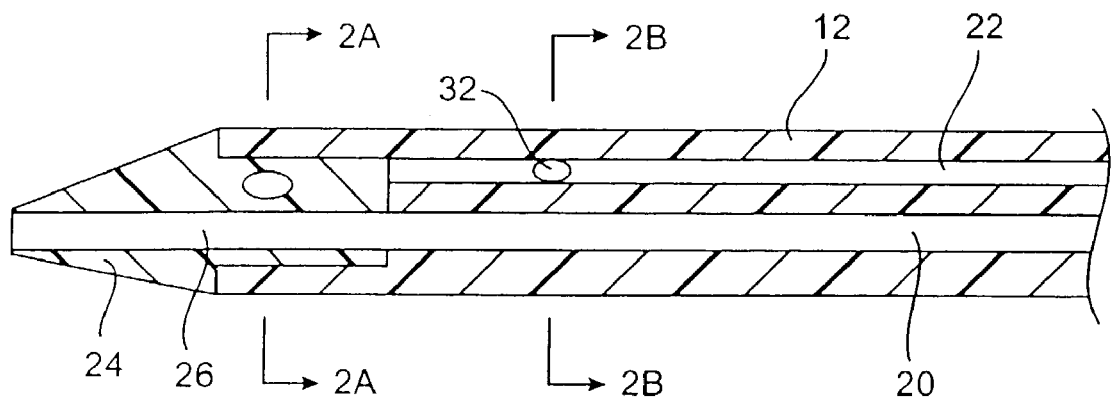
FIG. 2 is an axial sectional view of a distal end of the catheter of FIG. 1.
Figure 2A:
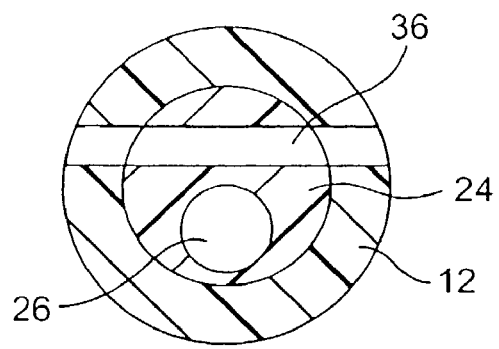
FIGS. 2A and 2B are cross-sectional views taken along lines 2A—2A and 2B—2B of FIG. 2, respectively.
Figure 2B:
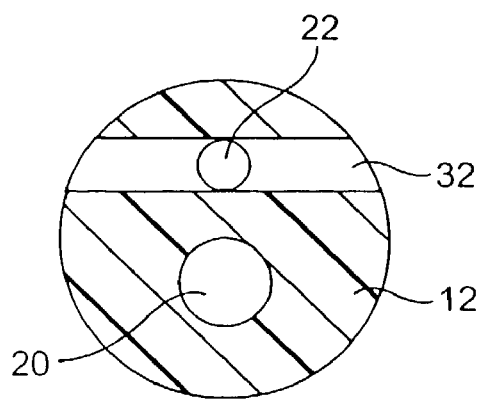

Referring now to FIGS. 2, 2A, 2B, an exemplary catheter body 12 has a guidewire lumen 20 which extends the entire length of the catheter body and at least one infusion lumen 22 which also extends the entire length of the catheter body. A nose cone 24 which is secured within the distal tip of the catheter body 12 and includes a lumen 26 which aligns with the guidewire lumen 20 in order to form a continuous passage which terminates in a guidewire port 28 in the proximal hub 16. The nose cone 24 may be tapered, squared, or otherwise formed so that it may facilitate inversion of and trauma to the vein being removed.

The infusion lumen 22 is blocked at its distal end by the nose cone 24. Thus, fluid which is introduced to the lumen 22 through an infusion port 30 on hub 16 will pass outwardly through the infusion port 32 (see FIG. 2B) of the catheter body 12. In other instances, however, the guidewire lumen may be modified to provide for infusion through the catheter body 12.

To permit suturing or tying of the venous segment over the distal end of the catheter 10, a suturing passage 36 is provided transversely through the catheter body and a portion of the nose cone 26, as best illustrated in FIG. 2A. In this way, the free end of the venous segment which has been severed from the vein (as illustrated hereinafter) may be attached to the catheter by suturing through the vein and then tying circumferentially around the vein and over the catheter body. Such suturing and tying will provide a very tight connection which is circumferentially uniform over the catheter body. Such uniform attachment permits the application of relatively large axial forces on the vein to permit removal of the vein without tearing the vein. Alternatively, the suture needle may be passed directly through the catheter body 12 without any special provision other than that it be penetrable by a needle or other device to pass the suture therethrough.

Figure 3:
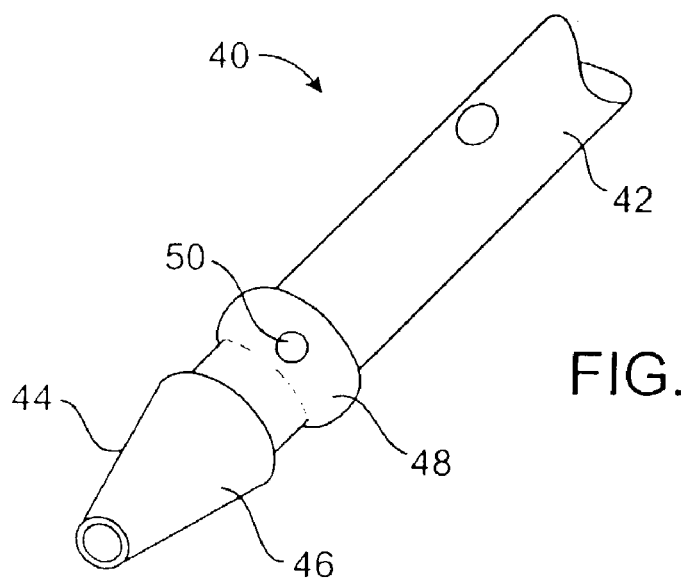
FIG. 3 is a perspective view of the distal end of a second embodiment of the pull catheter of the present invention.
Figure 3A:
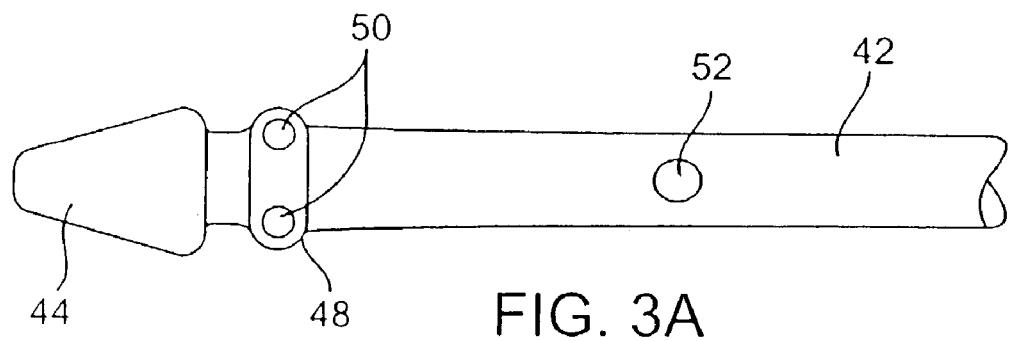
FIG. 3A is a side view of the distal end of the catheter of FIG. 3 shown at a first orthogonal orientation.
Figure 3B:
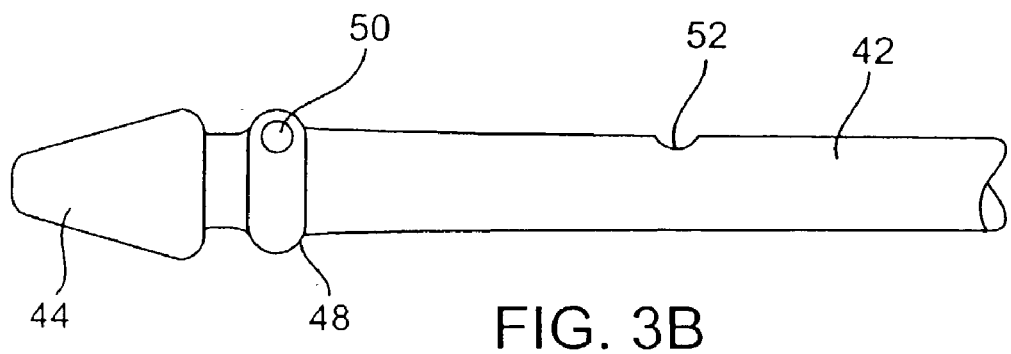
FIG. 3B is a side view of the distal end catheter of FIG. 3, shown at an orthogonal orientation which is 90° offset from that of FIG. 3A.

Catheter 10 may have a modified distal end including a trough or channel to further facilitate attachment of the free end of the venous segment being removed. Referring to FIGS. 3, 3A, 3B, a catheter 40 comprises a catheter body 42 with a distal end 44. A nose cone 46 has an enlarged proximal end relative to the diameter of the remainder of the catheter, and a second enlarged ring 48 is provided proximally of the proximal end of the nose cone. In this way, a trough or channel is created between the proximal end of the nose cone 46 and the distal end of the raised ring 48. A suturing passage 50 is provided laterally through the raised ring 48, and permits suturing of the venous segment therethrough. After suturing through the passage 50, the suture may be used to tie the vein onto the catheter by wrapping and tying in the region of the channel between the nose cone 46 and the raised ring 48. Catheter 40 will also include a perfusion port 52.

Figure 4:
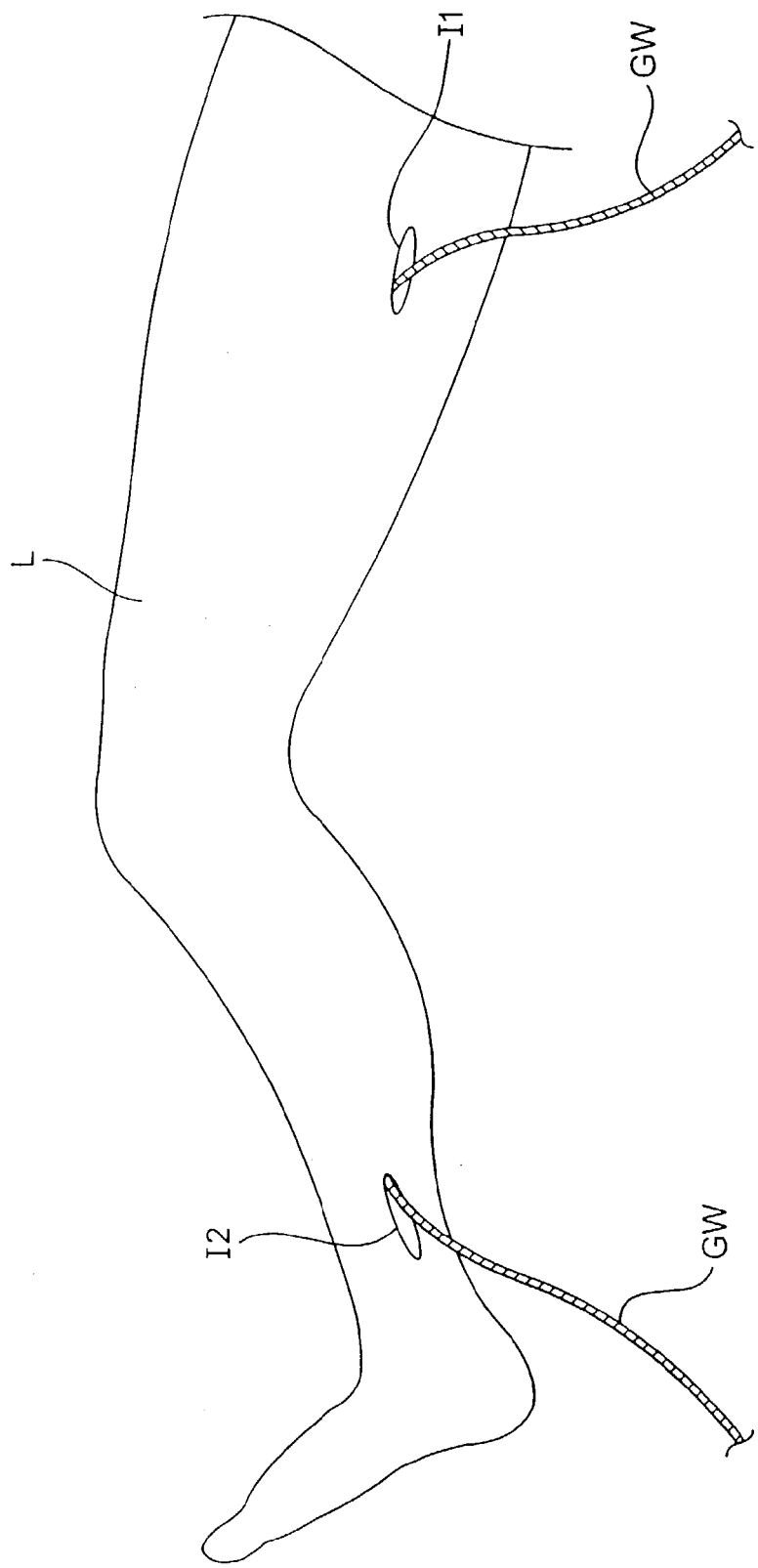
FIG. 4 illustrates the incision locations on a patient's leg which are useful for removing the greater saphenous vein in the methods of the present invention.

Referring now to FIG. 4, the removal of a saphenous vein SV from a patient's leg L will be described. An incision I1 is made over the greater saphenous vein in the patient's groin. A second incision I2 is made over the saphenous vein in the region of the patient's ankle. The incisions are typically surgical cutdowns, and the surgeon will have sufficient access to sever the saphenous vein at the locations I1 and I2. Thus, the length of the venous segment to be removed has now been defined by the two severed ends at the respective locations. After severing the ends, a guidewire GW is introduced through the venous segment to be removed between the locations I1 and I2.

Figure 5:
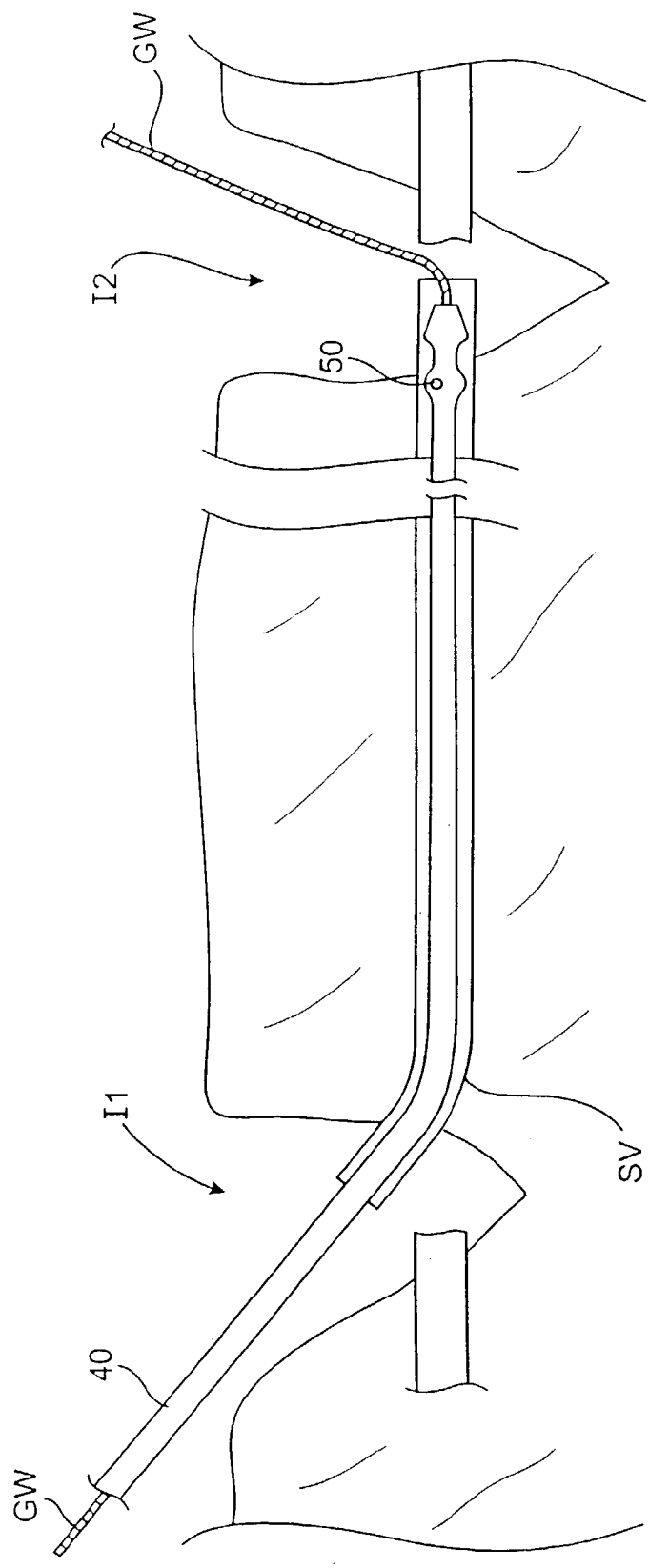
FIG. 5 illustrates the introduction of a pull catheter through the lumen of a venous segment to be removed according to the methods of the present invention.
Figure 5A:
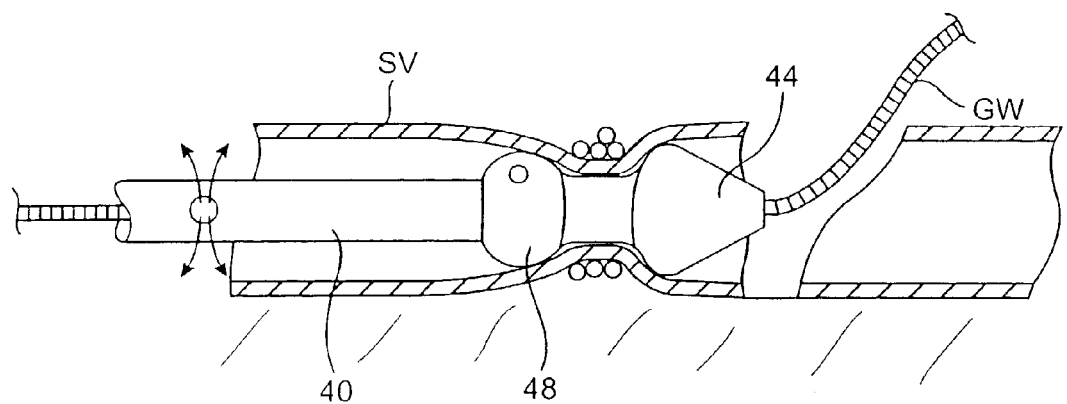
FIGS. 5A and 5B illustrates the initial steps of first securing an excised end of the venous segment to be removed to the pull catheter and of initially inverting the venous segment, respectively.

Referring now to FIG. 5, after the guidewire GW has been introduced, the pull catheter 40 is introduced over the guidewire from the first location I1 which has the larger lumen diameter. Catheter 40 is introduced until its distal end reaches the severed portion of the vein near the second location I2. At that point, as shown in FIG. 5A, suture is passed through suturing passage 50 and wrapped around the vein in the channel form between the nose cone 44 and ring structure 48. Optionally, saline or other medium may be infused into the lumen of the saphenous vein SV proximal to where the tying has occurred. Such saline infusion can facilitate inversion of the vein while the vein is being removed. After the vein has been removed, saline infusion will be used to help re-invert the vein, test the removed vein for leakage, and the like. In addition to saline infusion, the pull catheter may be provided with a balloon to initially dilate the vein to help free the remote end of the vein from the tissue bed and initiate inversion. The initial dilation is to increase diameter of vessel just proximal to where the tying has accrued so that the fold or inversion can start upon pulling the catheter.

Figure 5B:
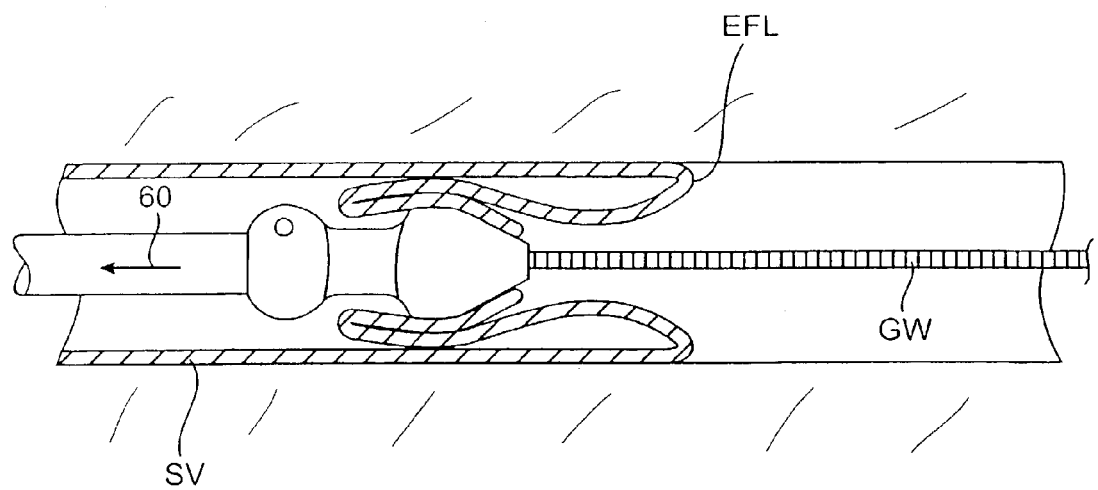

After the free end of the saphenous vein segment to be removed has been tied to the catheter 40, the catheter is drawn proximally back toward the first incision I1, as shown by arrow 60 in FIG. 5B. As the venous wall is drawn proximally, the vein inverts inwardly along an inversion line EFL.

Figure 5C:
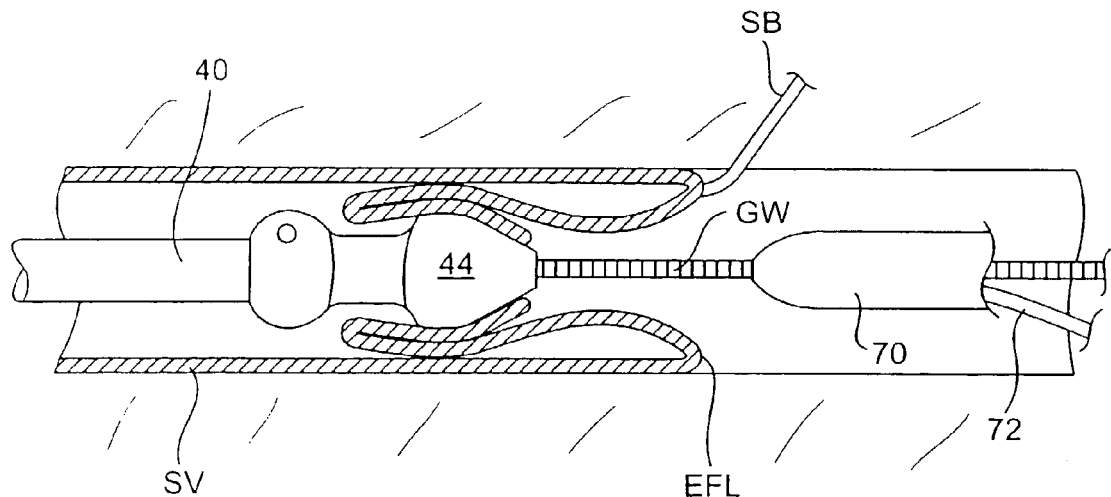
FIG. 5C illustrates the introduction of a catheter with a viewing scope to observe the vein being inverted.
Figure 5D:
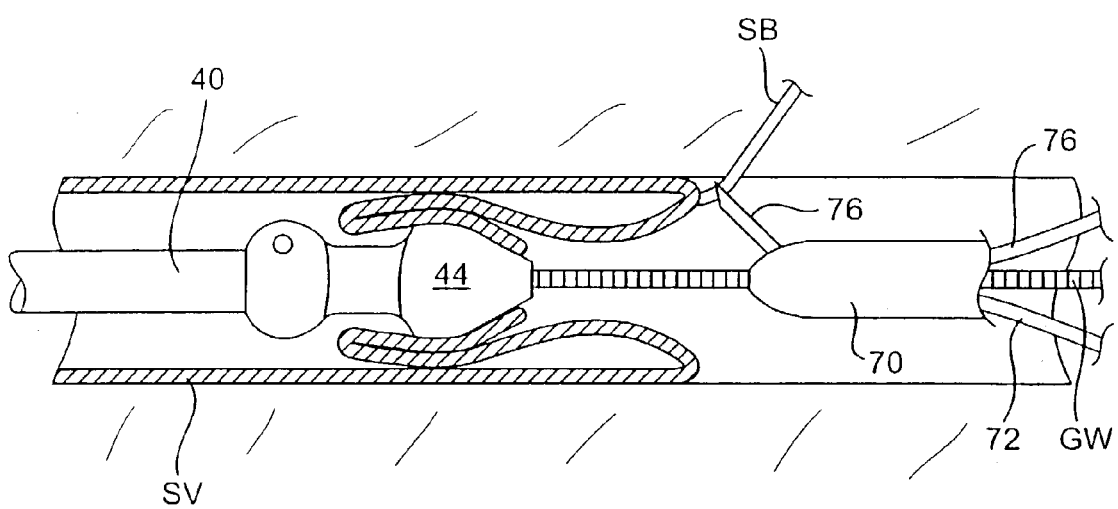
FIG. 5D illustrates the selective severing of a side branch under observation using the viewing scope.

The saphenous vein SV may continue to be withdrawn by pulling on the catheter 40. From time to time, however, the withdrawal of the vein may be impeded or stopped by the presence of a venous side branch SB, as shown in FIG. 5C. In some instances, it may be sufficient to simply pull on the catheter until the side branch SB breaks, typically near its attachment point to the wall of the saphenous vein SV. In other instances, however, it will be desirable to severe the side branch SB to facilitate continued removal of the saphenous vein. One approach for severing the side branches involves using a side branch management tool 70 having a blade 76, as shown in FIGS. 5C and 5D. The side branch management tool 70 may optionally have a transparent window and carry a viewing scope 72 to permit viewing of the inversion line EFL. The presence of the side branches will be quite apparent as they are pulled along the inversion line EFL, as shown in FIG. 5C. Once problematic side branches are identified, a cutting tool, shown schematically as a blade at 76 in FIG. 5D, may be advanced through the side branch management tool 70 to selectively severe the side branch SB.

Figure 6:
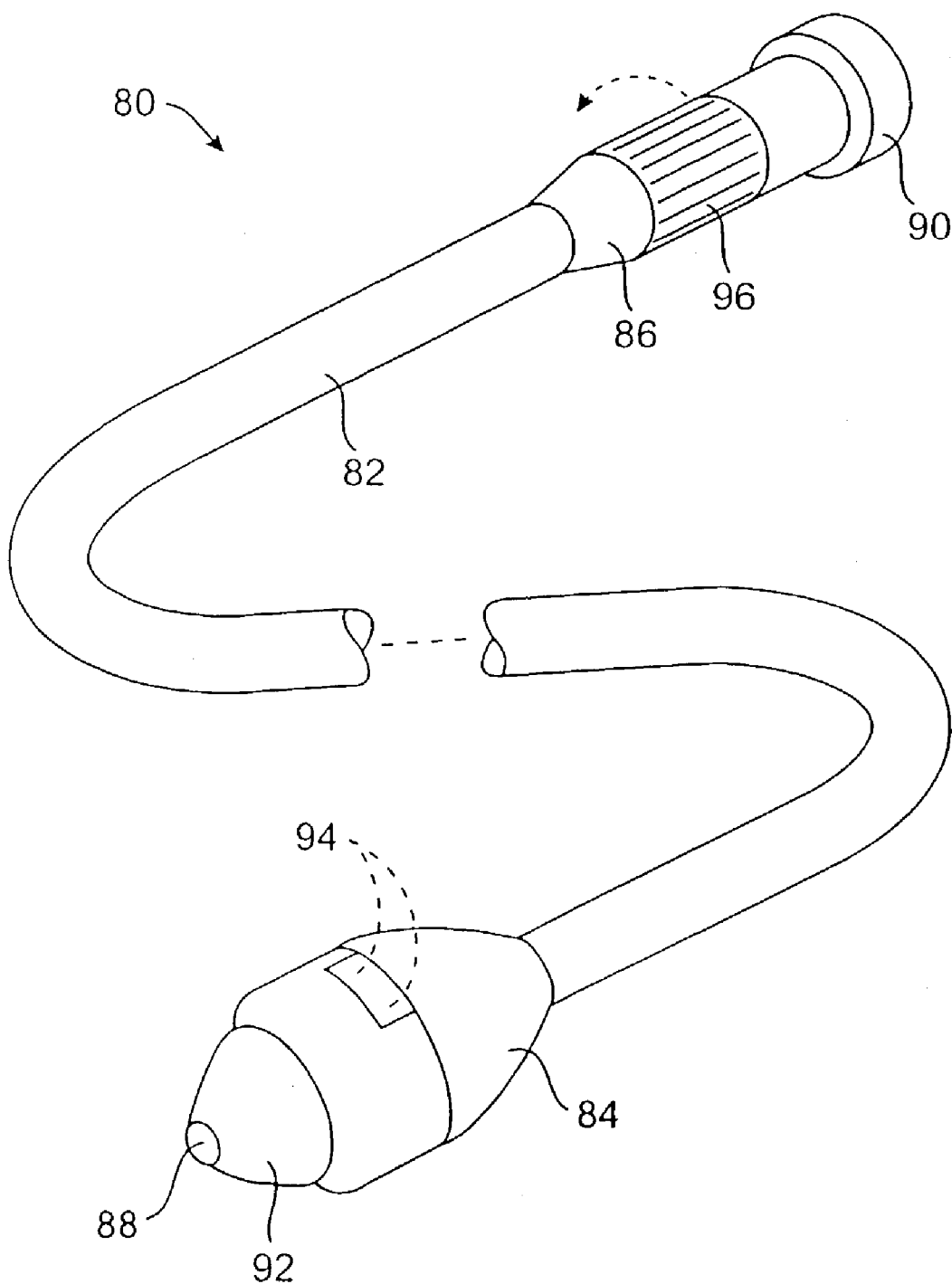
FIG. 6 is a perspective view of a blind side branch management tool having an actuable blade constructed in accordance with the principles of the present invention.

In addition to side branch management tools having instruments for both viewing and selectively severing side branches, the present invention also provides side branch management tools which are capable of acting "blindly," i.e., without direct visualization. A first example of such a blind tool is shown in FIG. 6. Side branch management tool 80 comprises a catheter body 82 having an acorn structure 84 at its distal end and a hub 86 at its proximal end. The tool is adapted to be introduced over a guidewire and includes guidewire lumen 88 at its distal end and a guidewire port 90 on the port 86. A blunt tip 92 is disposed at the distal end of the acorn structure 84 and an actuable blade 94 (shown in broken line) is adapted to extend radially outwardly and to traverse a generally circumferential path as the acorn 84 is rotated. The acorn 84 is rotatable by manually rotating a wheel 96 in the hub 86. The general dimensions of the catheter 80 have been set forth previously.

Figure 7A:
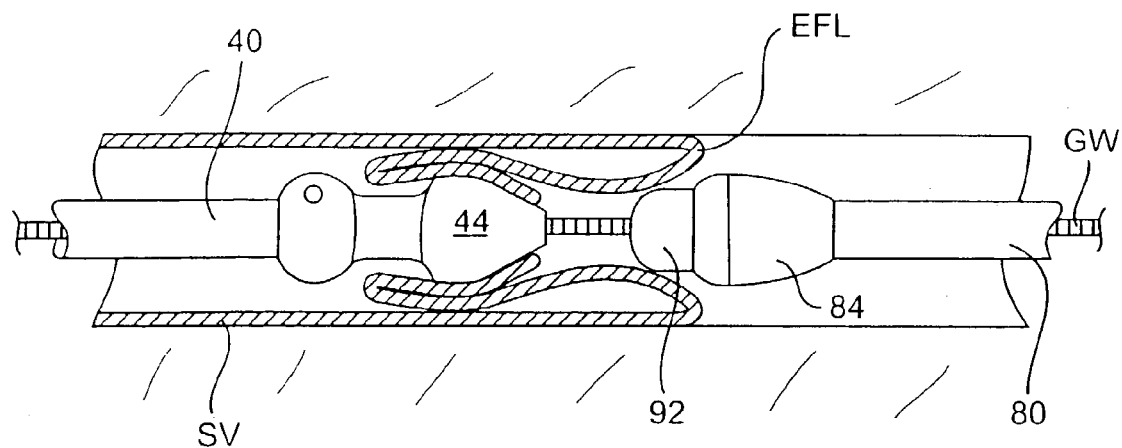
FIGS. 7A and 7B illustrates use of the catheter of FIG. 7 for tracking and serving a side branch attached to a venous segment being removed.
Figure 7B:
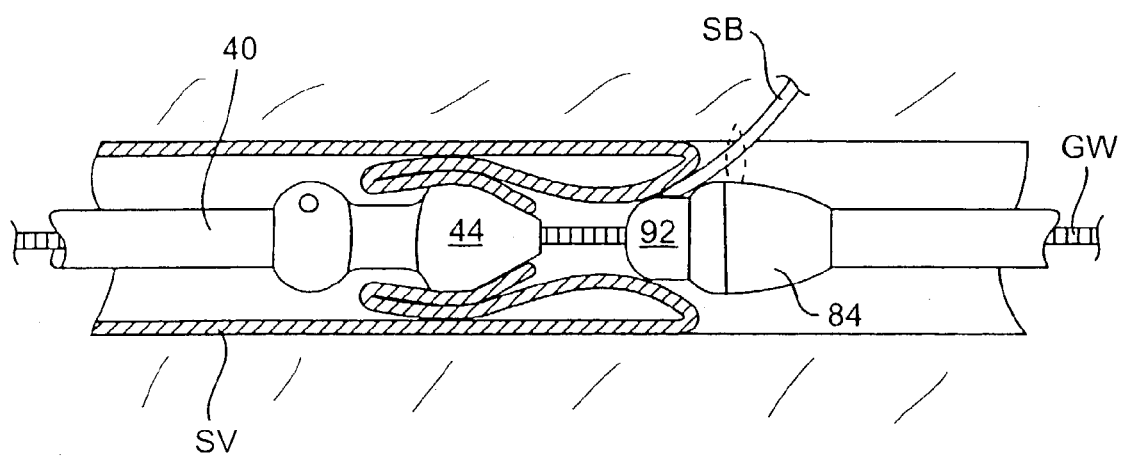

Use of the tool 80 for severing a side branch SB from the saphenous vein SV is illustrated in FIGS. 7A and 7B. The catheter 80 is introduced over the guidewire from the direction of the second incision I2 until the leading tip 92 engages the region of the saphenous vein SV which is being inverted, as shown in FIG. 7A. The distal end 92 is sized so that it can center within the inverting venous wall, allowing the catheter 80 to be advanced in unison with the receding inversion line EFL.

When the inversion line EFL reaches a side branch SB, as shown in FIG. 7B, the user will feel significant resistance to continue the withdrawal of the vein. If the resistance is sufficiently great, the user can choose to actuate the blade 94 to extend it radially and rotate the blade so that it circumscribes a circumferential path. In this way, the blade will encounter the side branch SB so that it may cut the side branch and free it from the venous segment which is being withdrawn. By properly spacing the blade away from the distal end 92 of the acorn structure 84, it can be assured that the blade remains behind the venous segment which is being removed so that it will not damage the vein.

Figure 8:
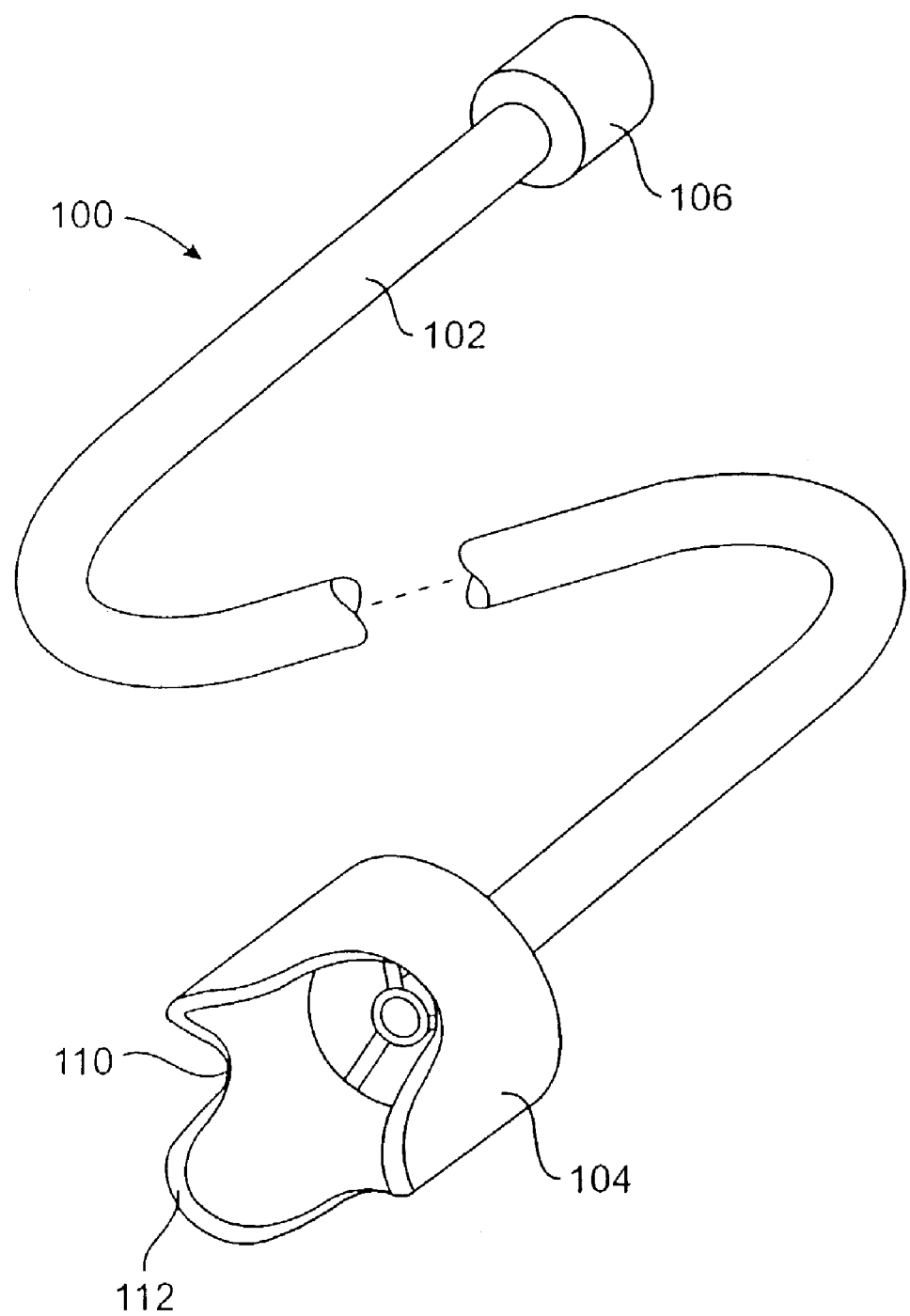
FIG. 8 illustrates another embodiment of an side branch management tool constructed in accordance with the principles of the present invention. The catheter of FIG. 8 includes a tubular excision blade.

An alternative side branch management tool 100 is illustrated in FIG. 8. Tool 100 includes catheter body 102 having a tubular cutter 104 at its distal end and a proximal hub 106 at it proximal end. Catheter body 102 has a guidewire lumen therethrough, the tubular cutting blade has a serpentine o-castellated structure where recessed portions 110 of the blades are sharpened with the leading portions of the blade 112 preferably being blunt.

Figure 9A:
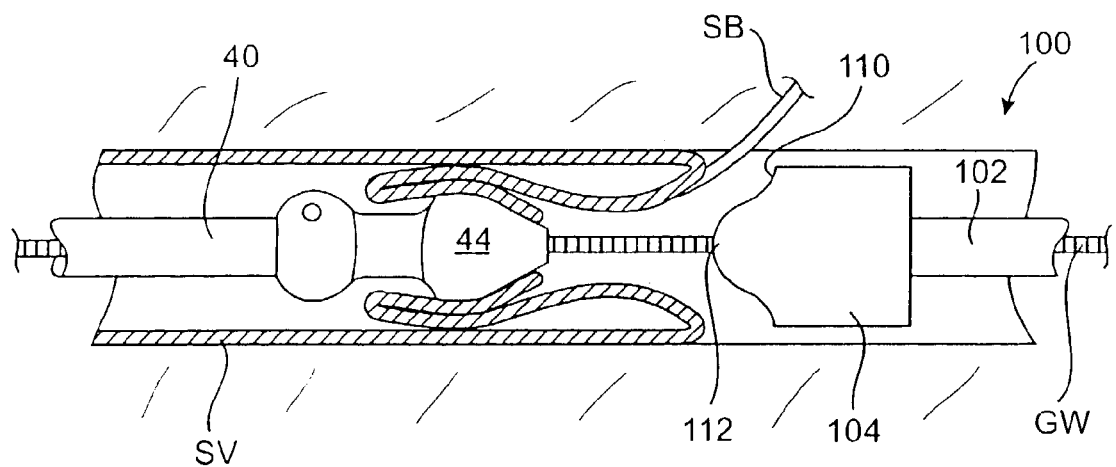
FIGS. 9A and 9B illustrate the use of the side branch management tool of FIG. 8 for cutting side branches from the venous segment being removed.
Figure 9B:
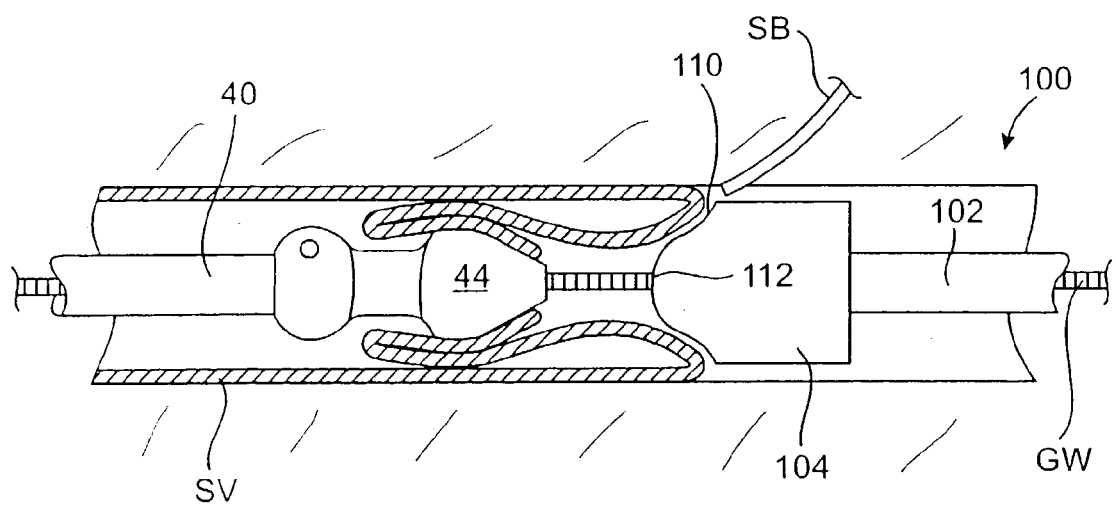

The side branch management tool 100 may be used to blindly severe side branches SB from the saphenous vein SV as it is withdrawn, as shown in FIGS. 9A and 9B. The catheter 100 is advanced from the second incision I2, generally as described above with reference to the other side branch management tools. The saphenous vein SV is withdrawn by catheter 40 until resistance to withdrawal caused by the presence of a side branch SB is felt by the surgeon. The catheter 40 is then advanced and slowly rotated so that the leading edges 112 self-align to blade 104 so that the sharpened recess portions 110 engage the side branch SB, as shown in FIG. 9A. The blade 104 is then advanced so that the sharpened sections 110 severe the side branch SB, and the pull catheter can then be further withdrawn until the next side branch is encountered or the venous segment is entirely removed.

Figure 10:
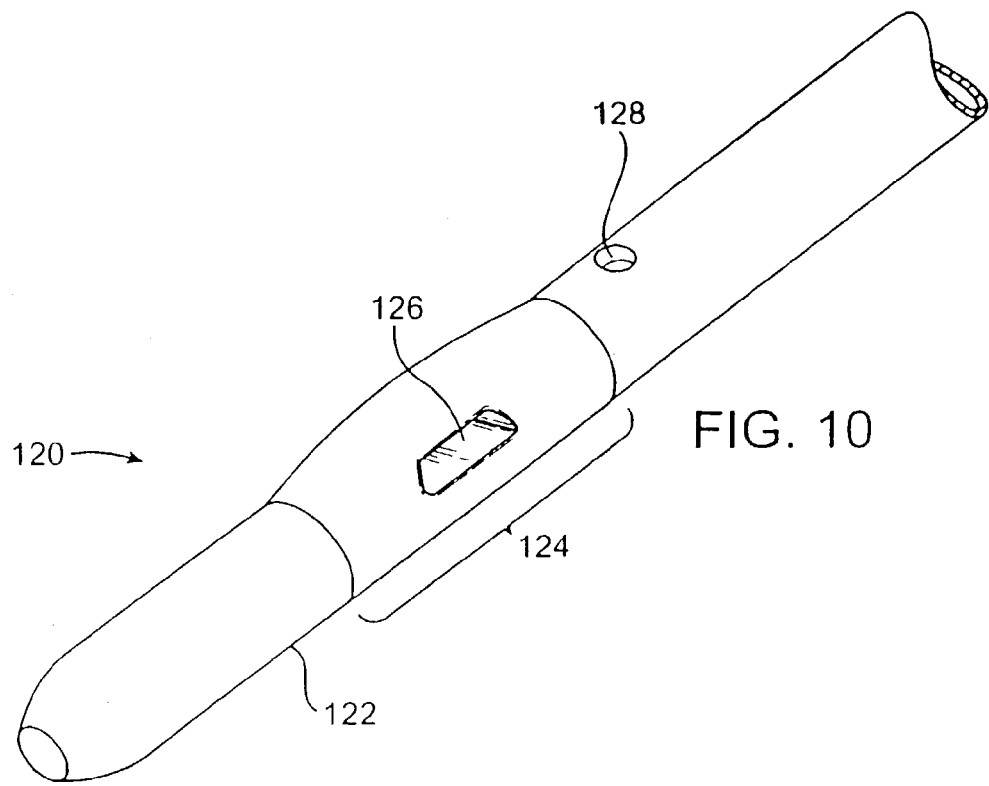
FIGS. 10–12 illustrate alternative distal end constructions for the pull catheters of the present invention.
Figure 11:
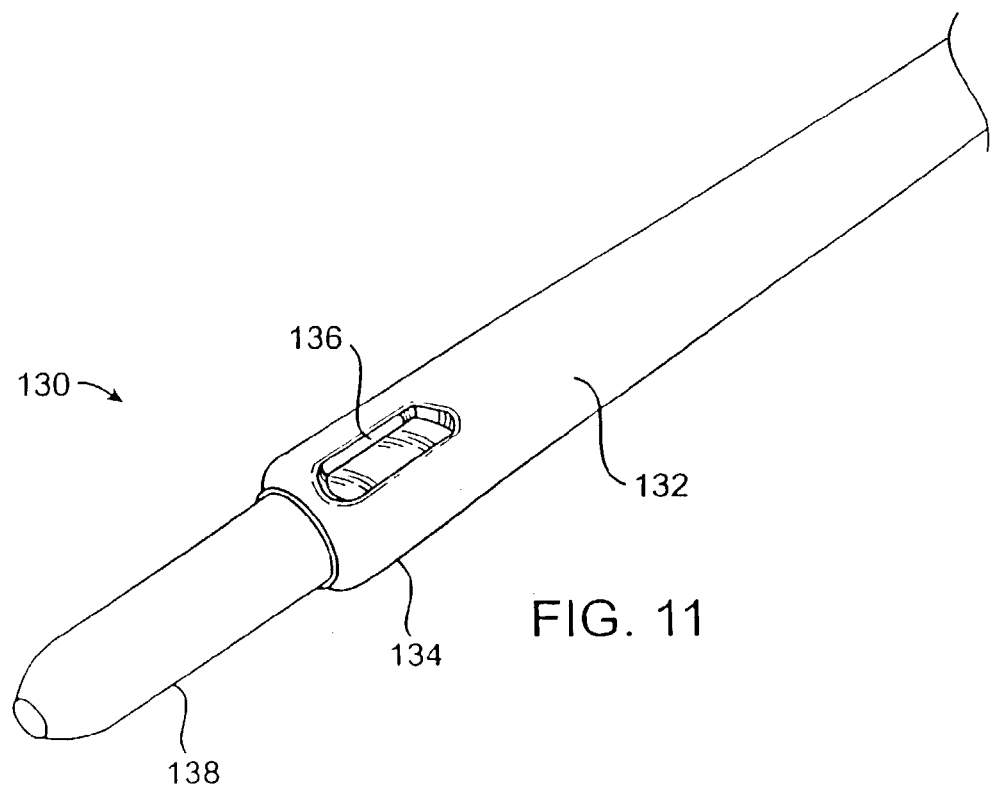
Figure 12:
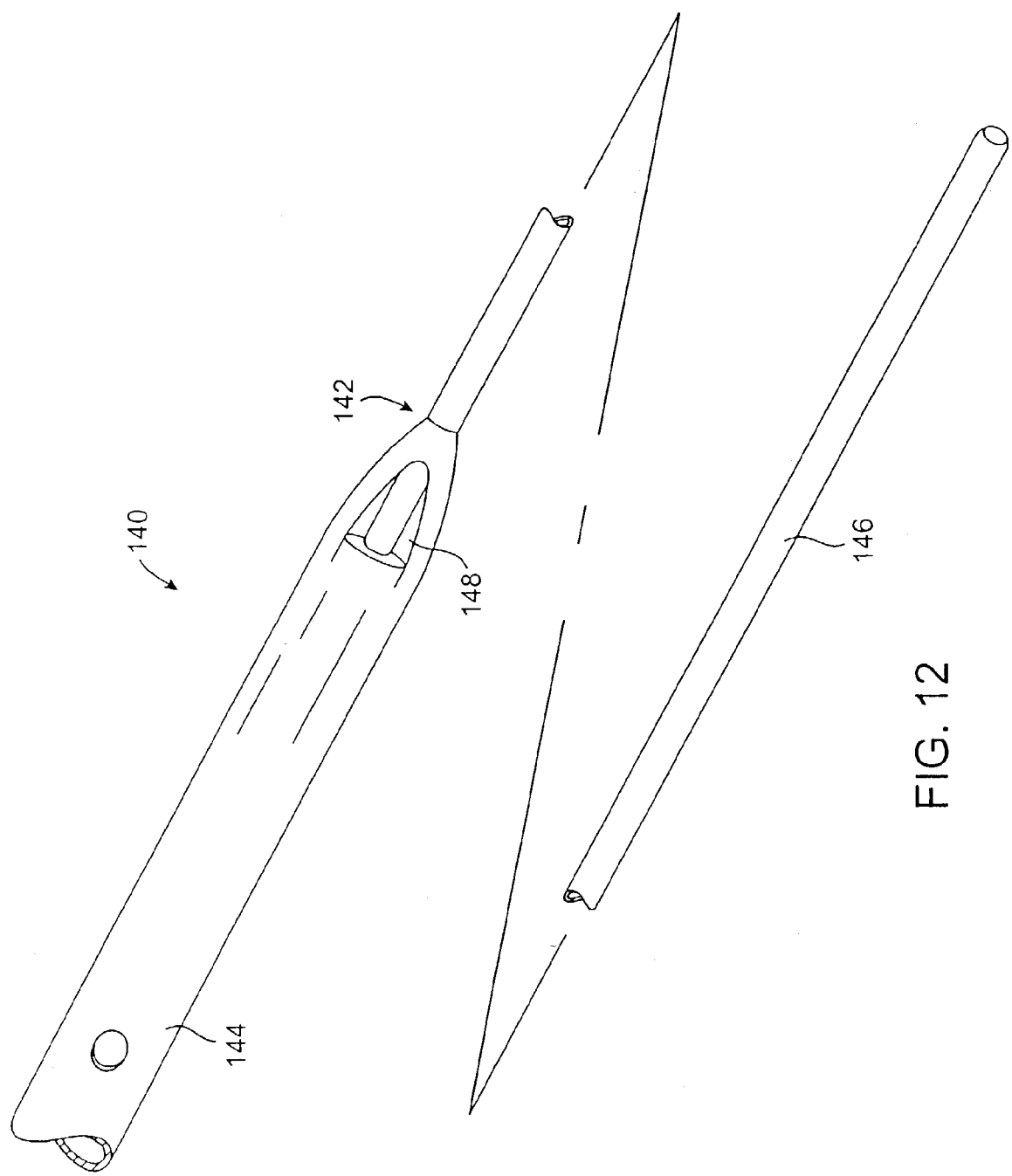
Figure 13:
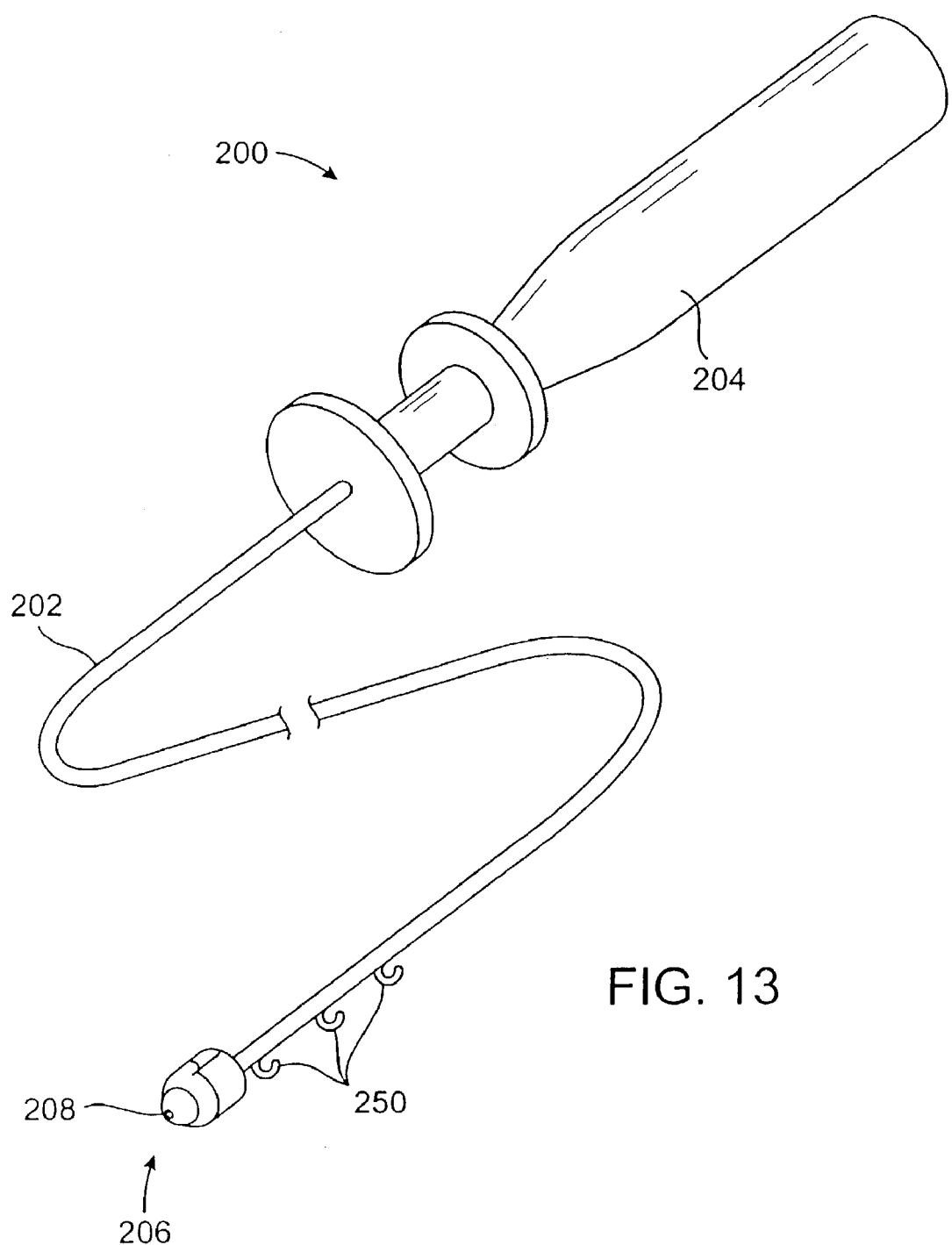
FIG. 13 illustrates a specific embodiment of the side branch management tool of the present invention having a notched acorn structure at its distal end.

Referring now to FIGS. 10–12, alternative structures for the distal end of the pull catheter of the present invention will be described. In FIG. 10, a pull catheter 120 has a distal end 122 with an enlarged or expanded region 124 having an aperture 126 for receiving suture to attach a dissected venous wall. Port 128 is provided for selectively infusing saline or other liquid medium which can aid in re-inversion of the vessel.

In FIG. 11, a pull catheter 130 has a distal end 132 which has a radially expanding flare which terminates in a shoulder 134 having a suture-receiving aperture 136 formed therein. A smaller diameter nose cone 138 projects distally from the shoulder 134 which can assist in initiating inversion of the vessel. The ligature knot circumferentially secures the vessel around the smaller diameter nose, pre-disposing the vein to be inverted.

An additional pull catheter 140 is illustrated in FIG. 12. The pull catheter 140 has a transition region 142 disposed between a main catheter body 144 and a narrow diameter distal extension 146. Aperture 148 is formed near the transition 142 and is suitable for receiving suture for tying and attaching a dissected end of the vein being removed. The purpose of the distal extension 146 is to assist in management of the vein after it has been removed from the tissue bed. In particular, as the pull catheter of 140 is drawn proximally, e.g., as shown in FIG. 5B, in connection with pull catheter 40, the vein will extend over the distal extension 146. Thus, when the vein has been fully everted, the distal extension (which will usually have a length approximately equal to that of the main portion of the catheter body 144) will lie within the length of the removed venous segment. After the pull catheter 140 and removed venous segment are completely removed from the patient, it will be appreciated that the distal extension 146 will provide a linear support for the vein, thus facilitating manipulation of the vein. In particular, preparation of the vein, such as trimming and optional closure of the side branches which remain, will be facilitated. Presence of the venous segment over the distal extension 146 will also help with reinversion of the vein after the interior (which is exposed outwardly while the vein is inverted) has been prepared.

Figure 14:
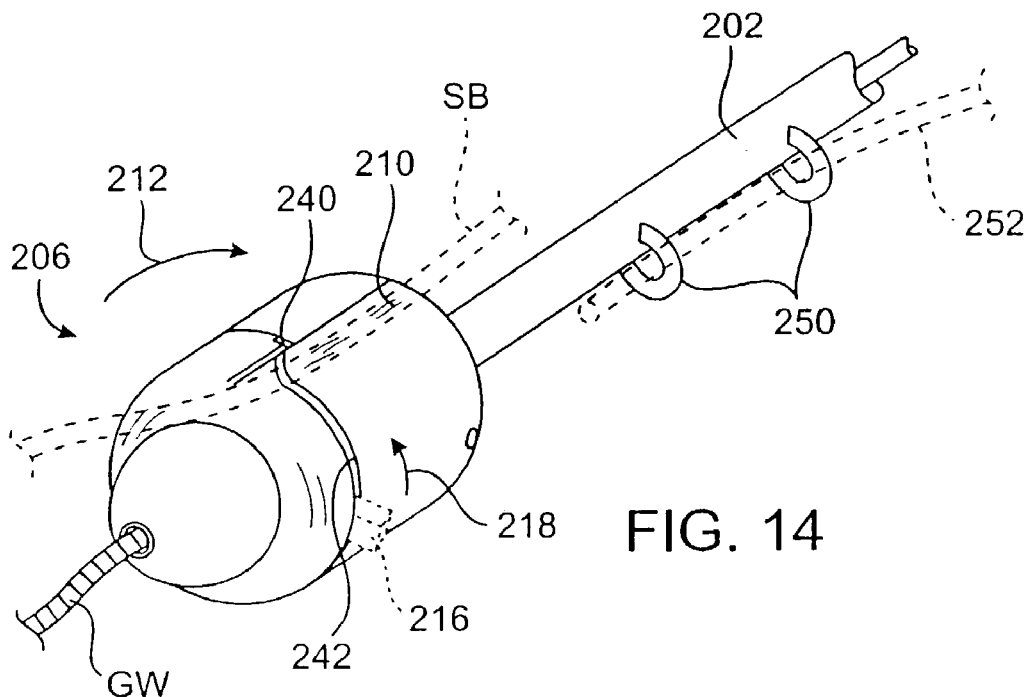
FIG. 14 is a detailed view of the notched acorn structure of FIG. 13.
Figure 15:
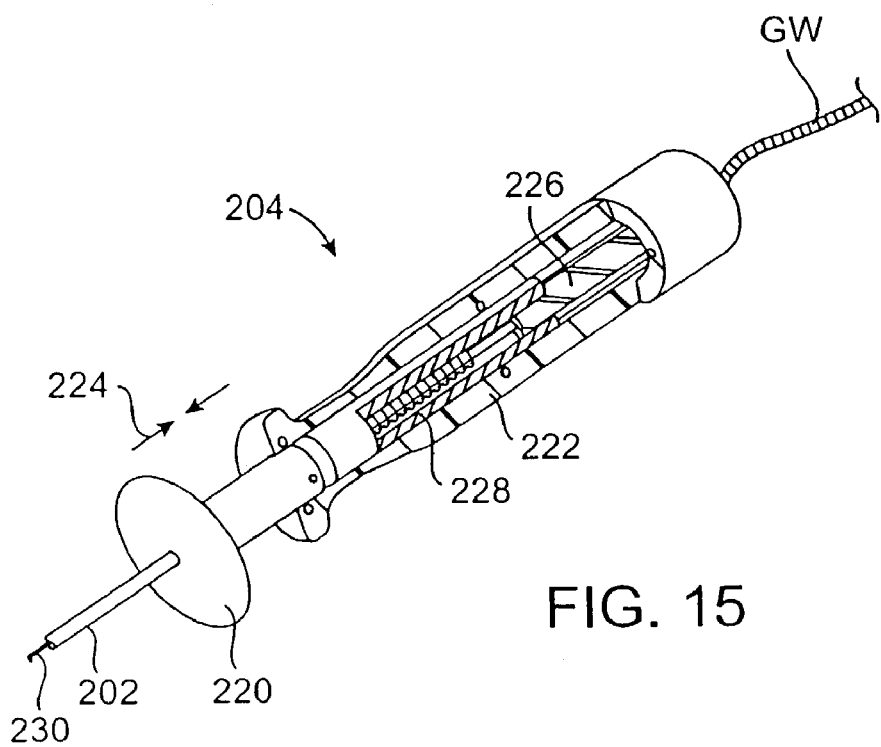
FIG. 15 is a detailed view, with portions broken away, of the handle of the side branch management tool of FIG. 13.

Referring now to FIGS. 13 to 16A–16C, a presently preferred construction of a side branch management tool similar to tool 80 will be described. The tool 200 comprises a catheter body 202 having a handle 204 at its proximal end and a notched acorn structure 206 at its distal end. The acorn structure 206 is similar to that described previously for side branch management tool 80, but further includes a stop or notch structure 210 which facilitates engagement and tensioning of the side branch prior to cutting. As shown in FIG. 14, the stop or notch structure 210 can engage a side branch SB (shown in broken line) by rotating the acorn structure 206 in the direction of arrow 212. Once the side branch SB has been engaged and tensioned, a blade 216 can be actuated to extend radially outwardly and rotate in the direction of arrow 218 to seven side branch.

The stop or notch structure 210 illustrated in FIG. 14 has a number of advantages. In particular, it is relatively smooth and free from abrupt changes or features which would hinder advancement of the catheter 200 through the venous lumen. It will be appreciated, however, that a variety of other structures, such as hooks, pins, loops, or the like, can also be used to selectively engage and tension a side branch in a manner similar to the illustrated stop or notch 210.

Figure 16A:
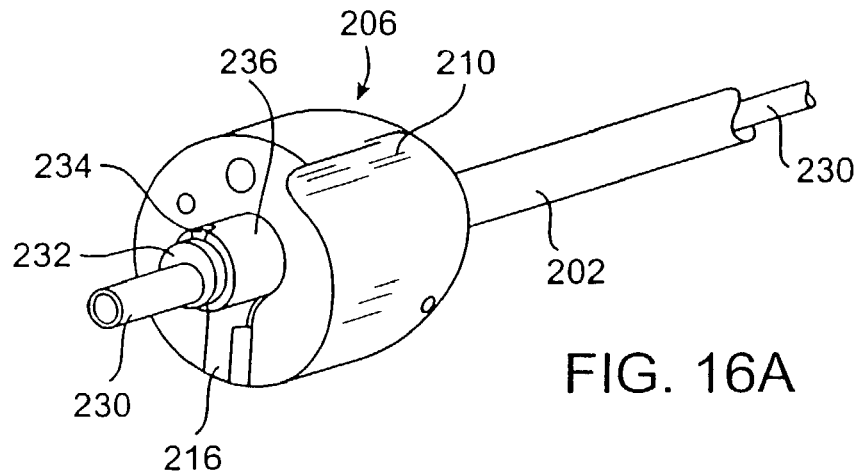
FIGS. 16A–16C illustrate actuation of a blade and the notched acorn structure of the catheter of FIG. 13.
Figure 16B:
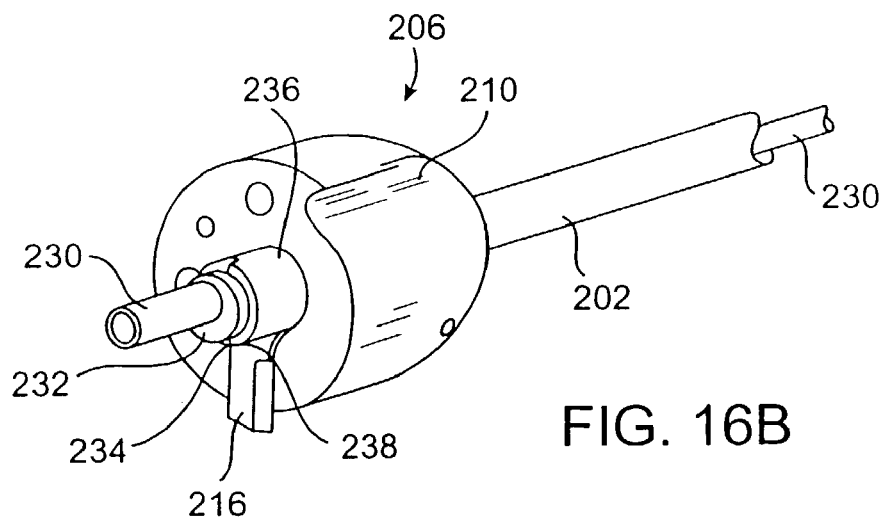
Figure 16C:
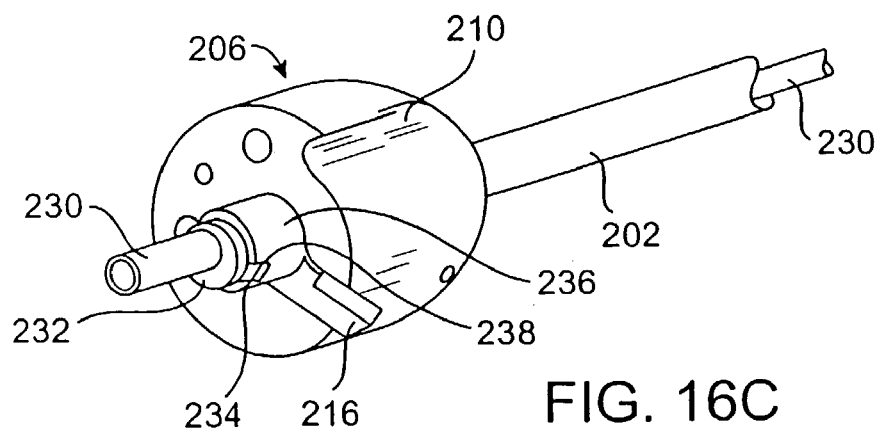

The blade 216 is preferably fully retracted within the notched acorn structure 206 prior to deployment. As shown in FIGS. 15 and 16A–16C, the preferred mechanism for actuating blade 216 will be described. The proximal handle 204 includes a distal button 220 and proximal gripping portion 222. A user may hold the gripping portion 222 in one hand with the fingers placed over the button 220 so that the button and gripping portion can be selectively closed in the direction of arrows 224. Such selective closure translates a spirally moved cylinder 226 relative to a fixed sleeve 228 having pins which travel in the grooves. This motion causes the cylinder 226 to rotate about its axis. The cylinder 226, in turn, is coupled to a rod 230 which extends from the cylinder, through the catheter body 202, and into an eccentrically mounted cylinder 232 having a radially extending pin 234, as best seen in FIG. 16A. The eccentric cylinder 232 is mounted in a ring 236 which is rotatably mounted within the notched acorn structure 206. As the user actuates the handle 204 to rotate rod 230, the eccentric cylinder 232 first rotates to radially extend the blade 216, as shown in FIG. 16B. Once the cylinder 232 has been rotated 180°, as shown in FIG. 16B, the pin 234 engages a shoulder structure 238 on the rotatable ring 236. In this way, further rotation of the rod 230 causes the eccentric cylinder 232 to rotate the ring 236, and thus the blade 216, as illustrated in FIG. 16C. The blade 216 can be fully rotated to reach the notch 210 and stops travel when it engages rim 240 of slot 242 (FIG. 14) which accommodates travel of the blade. In this way, the blade can fully pass through the side branch SB which is held in the stop or notch 210.

Any of the side branch management tools of the present invention may incorporate viewing scopes, CCD's, or other imaging capability. For example, side branch management tool 200 may optionally be provided with clips 250 (shown in FIGS. 13 and 14 only) for removably attaching a fiberoptic viewing scope 252, shown in broken line in FIG. 14. The side branch management tools, of course, could also be provided with integrated optics or other viewing systems within the scope of the present invention.

Figure 17:
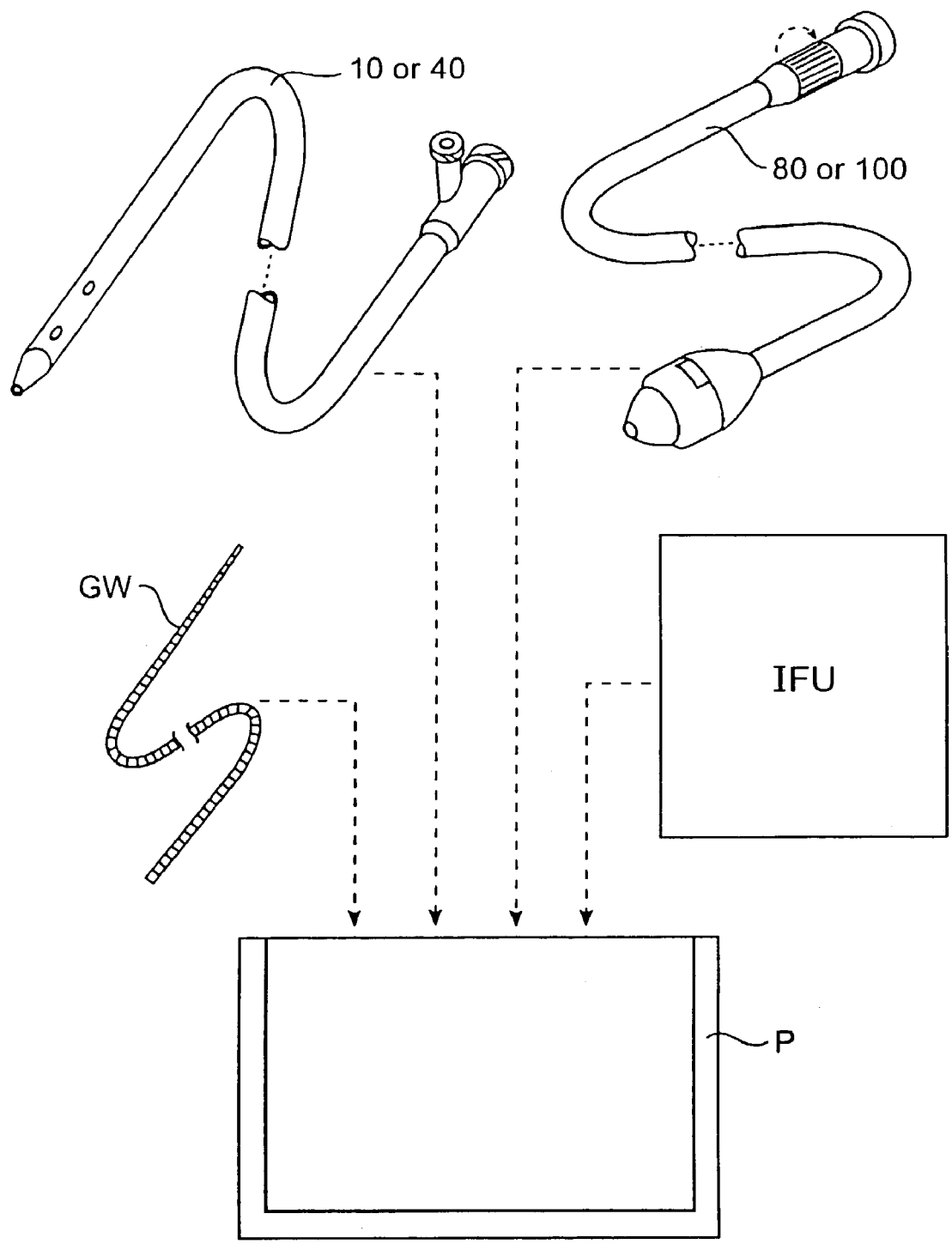
FIG. 17 illustrates a kit constructed in accordance with the principles of the present invention.

Referring now to FIG. 17, systems according to the present invention will comprise the pull catheter 10 or 40, an side branch management tool 80 or 100, and a guidewire GW. The systems will typically be packaged together in a conventional medical device package B, such as pouch, tube, tray, box, or the like. The components may be packed separately within individual packages within the larger packages B. In all instances, the components are preferably sterilized, either by heat, ethylene oxide, or other conventional sterilant. Kits according to the present invention will further comprise instructions for use IFU setting forth any of the methods described above.

Referring now to FIGS. 18A–18G, the creation of an arteriovenous fistula (AVF) between a basilic vein and a brachial artery in a patient's shoulder will be described. The basilic vein BV is exposed through an incision I1 near the patient's elbow. The vein is divided to expose a distal end DE and a guidewire GW is introduced into the venous lumen and advanced to a location at or near the superior vena cava-right arterial junction (not shown).

Figure 18A:
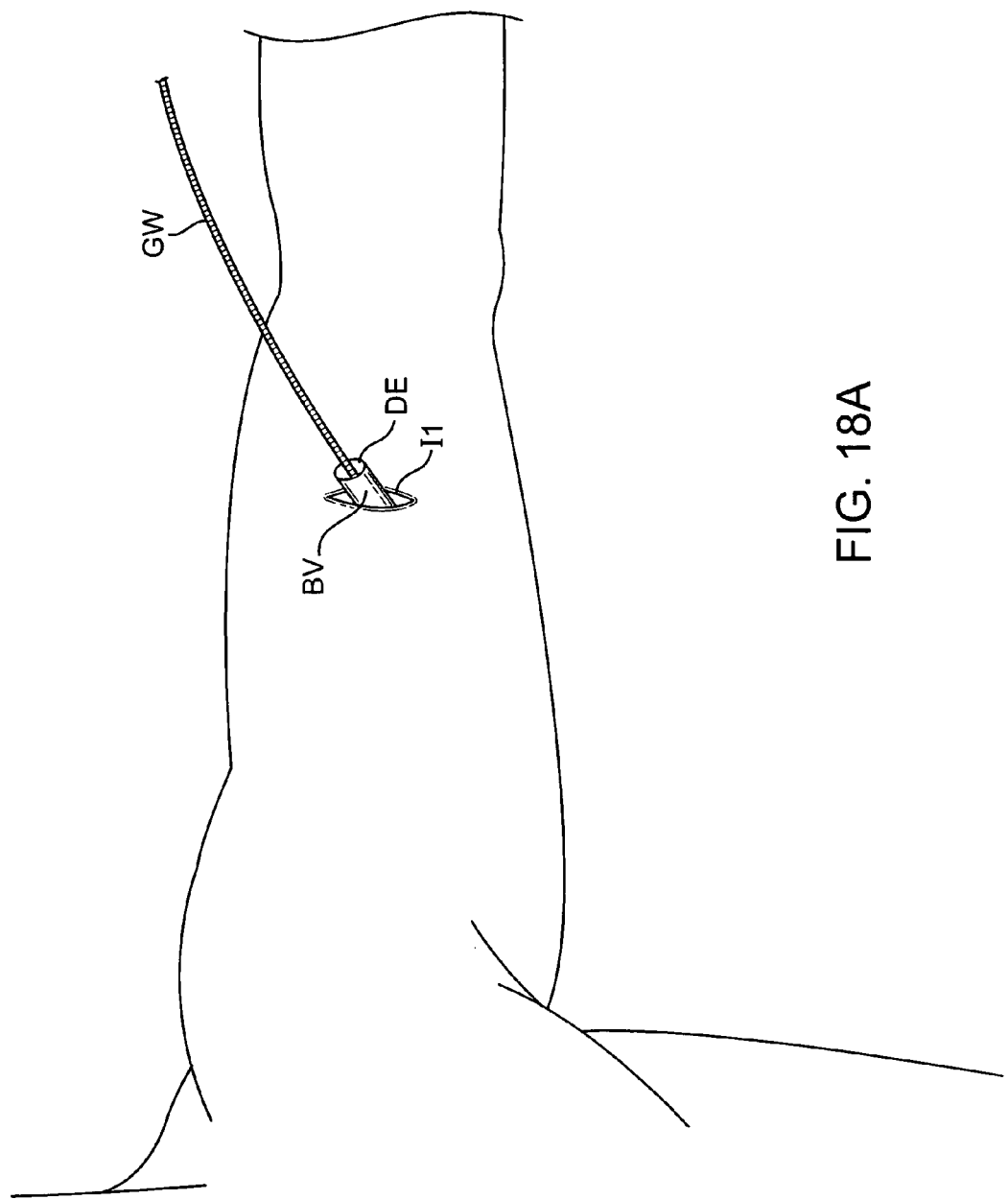
FIGS. 18A–18G illustrate a method according to the present invention for creating an arteriovenous fistula between a basilic vein and a brachial artery in a patient's shoulder.
Figure 18B:
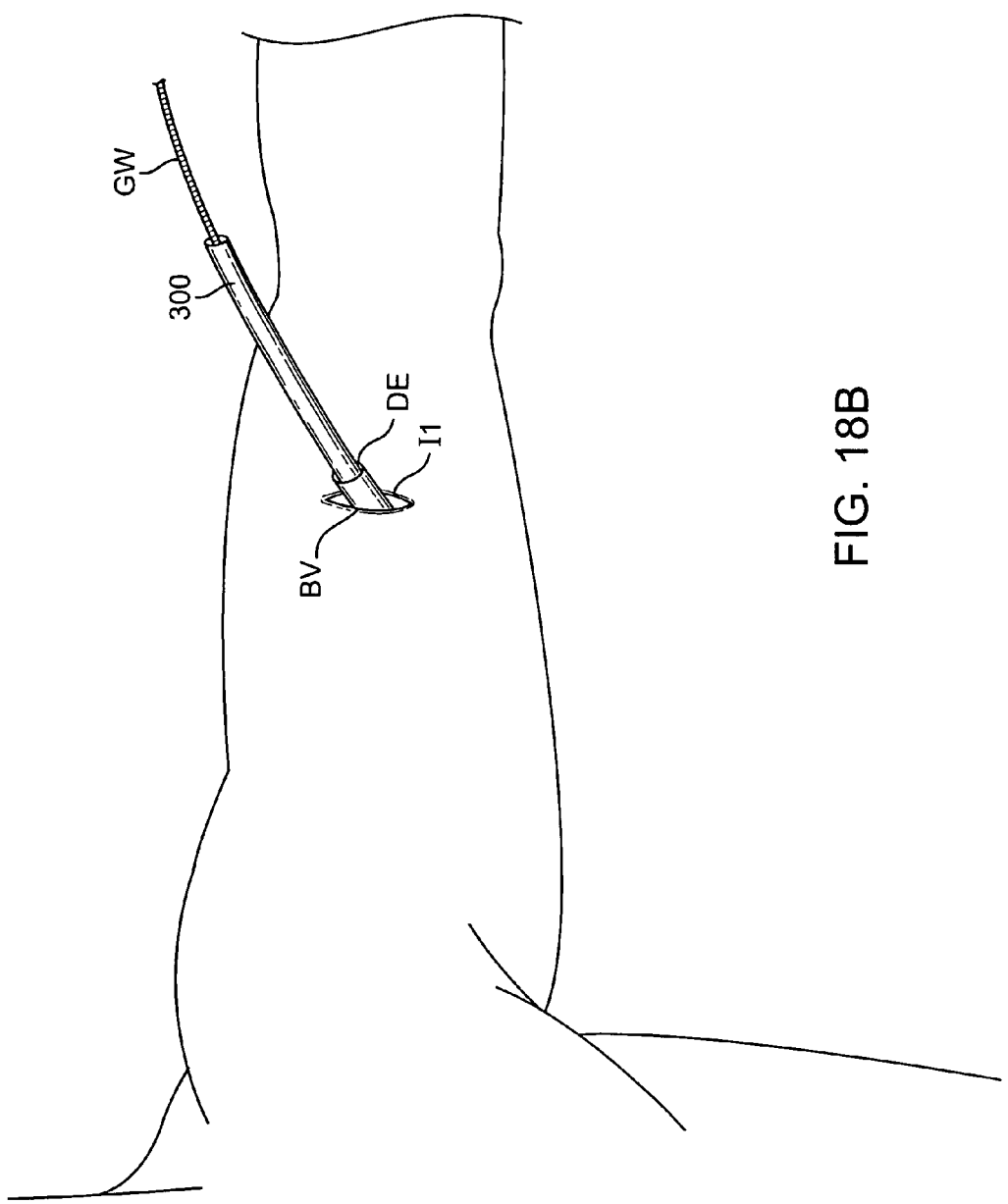
Figure 18C:
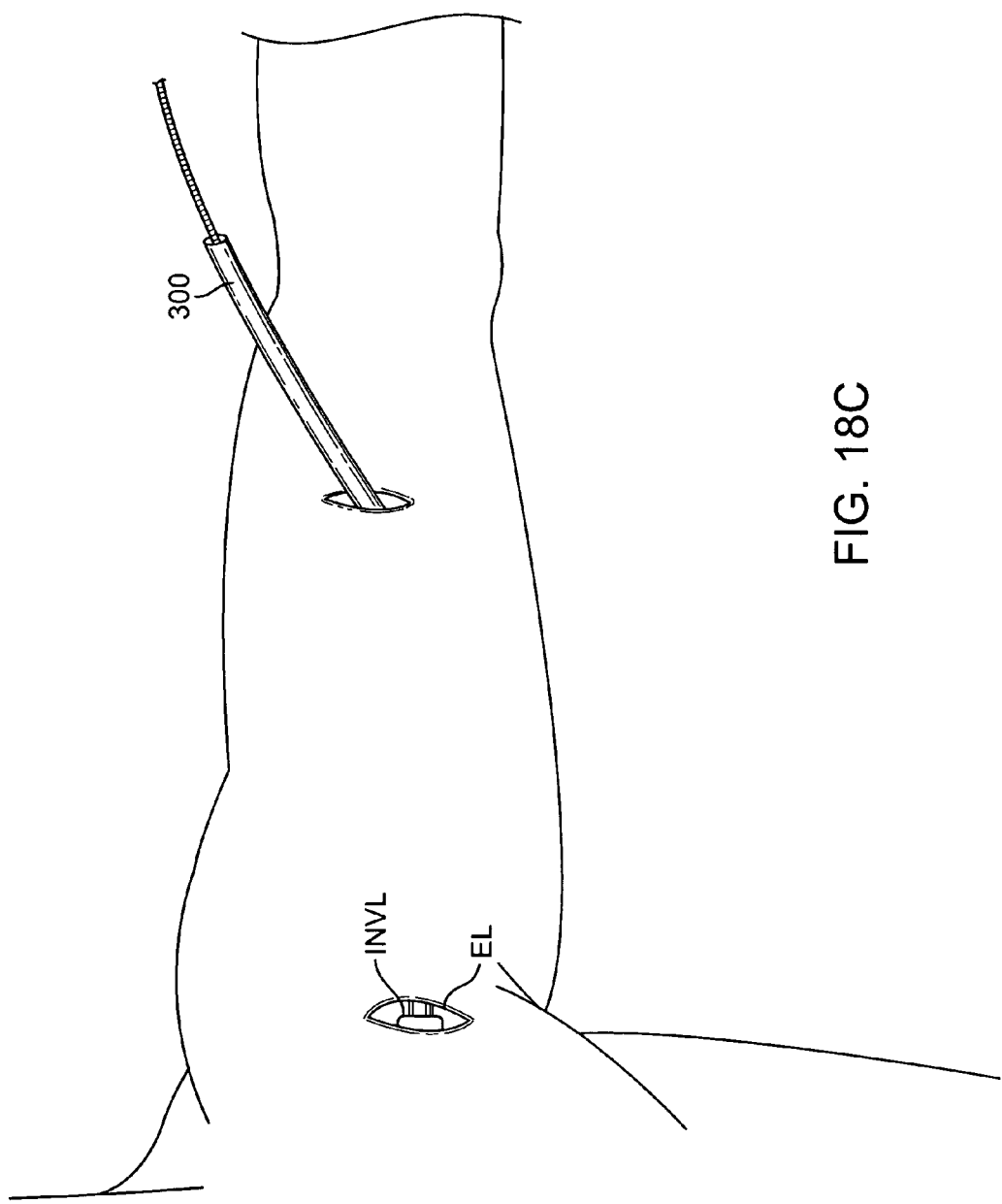

In FIG. 18B, a push catheter 300 is advanced proximally over the guidewire GW and through the lumen of the basilic vein. The distal end DE of the basilic vein is attached near the leading end of the push catheter 300 and the vein is inverted as the catheter is advanced. As the push catheter 300 is advanced, an inversion line INVL moves in a proximal direction toward the patient's shoulder. The push catheter 300 will be advanced until the inversion line INVL reaches an exposure location EL located near the deltopectoral groove in the patient's shoulder, as shown in FIG. 18C. At this point, the leading end of the catheter 300 will have advanced close to the junction between the superior vena cava and the right arterial junction (not shown). It is an advantage that throughout the catheter advancement, the endothelium of the vein always remains protected inside the venous lumen. Side branches that are felt as resistances when pushing the catheter 300 forward are localized, clipped, and divided under direct vision using small counter incisions when necessary.

Figure 18D:
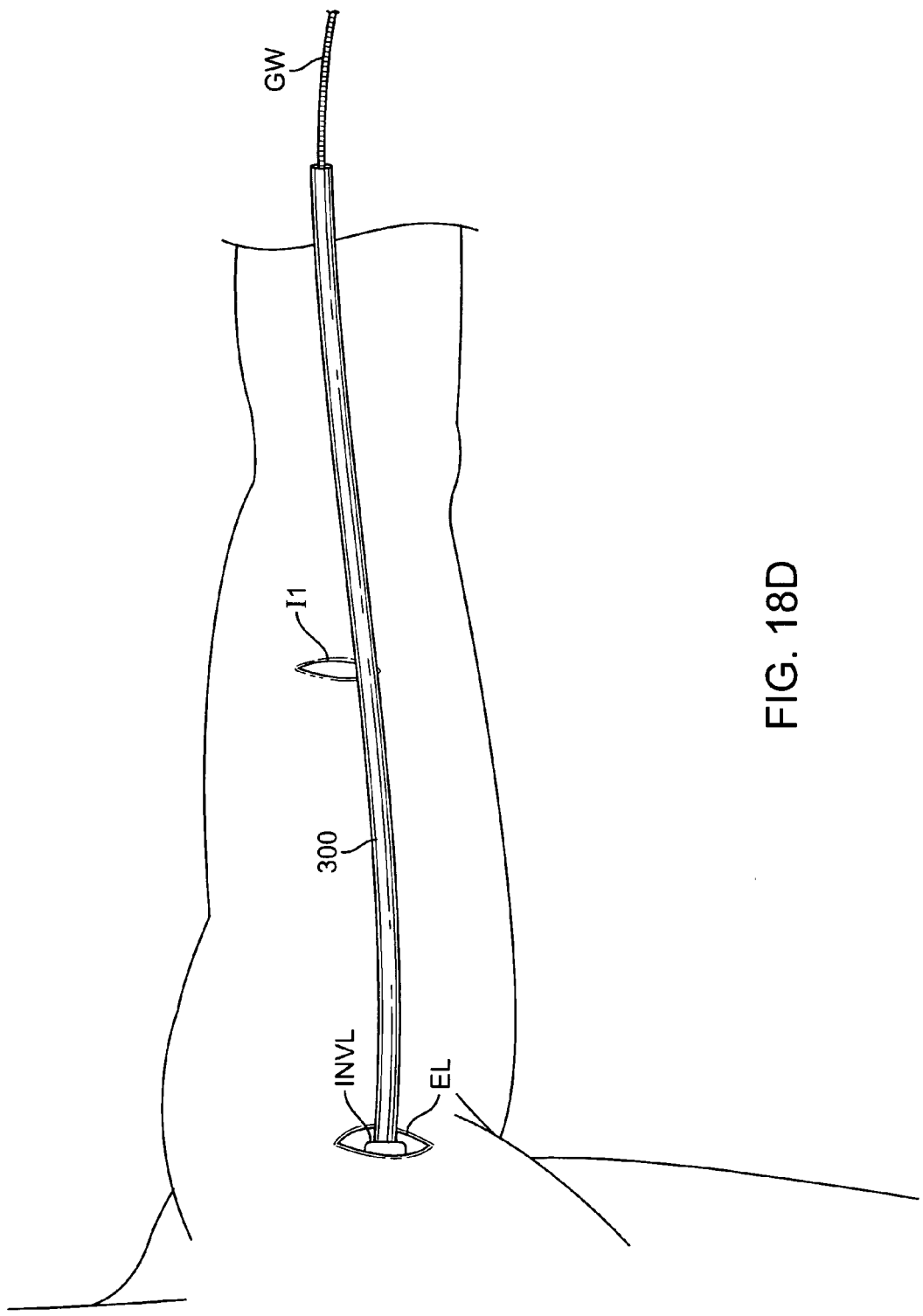
Figure 18E:
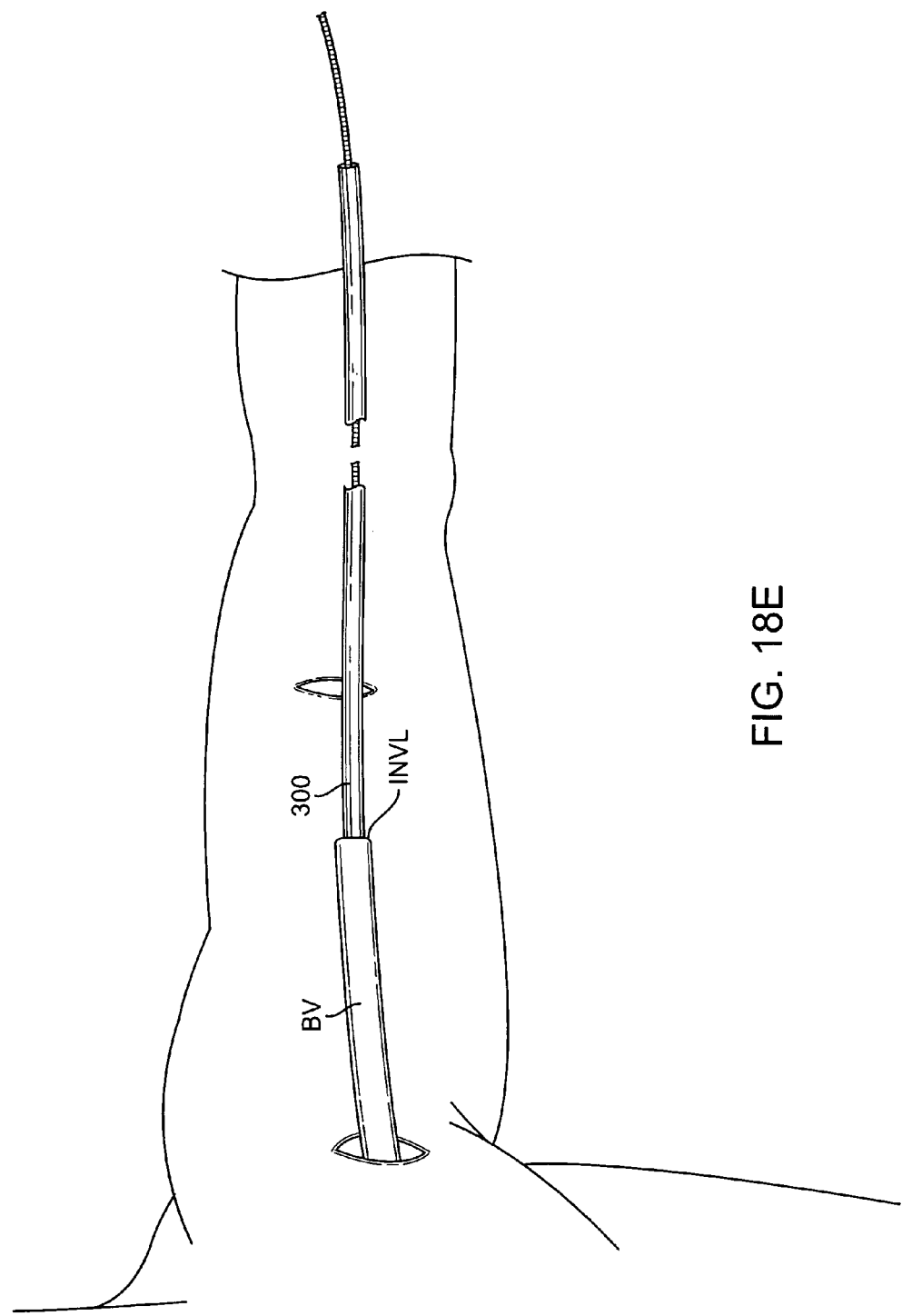
Figure 18F:
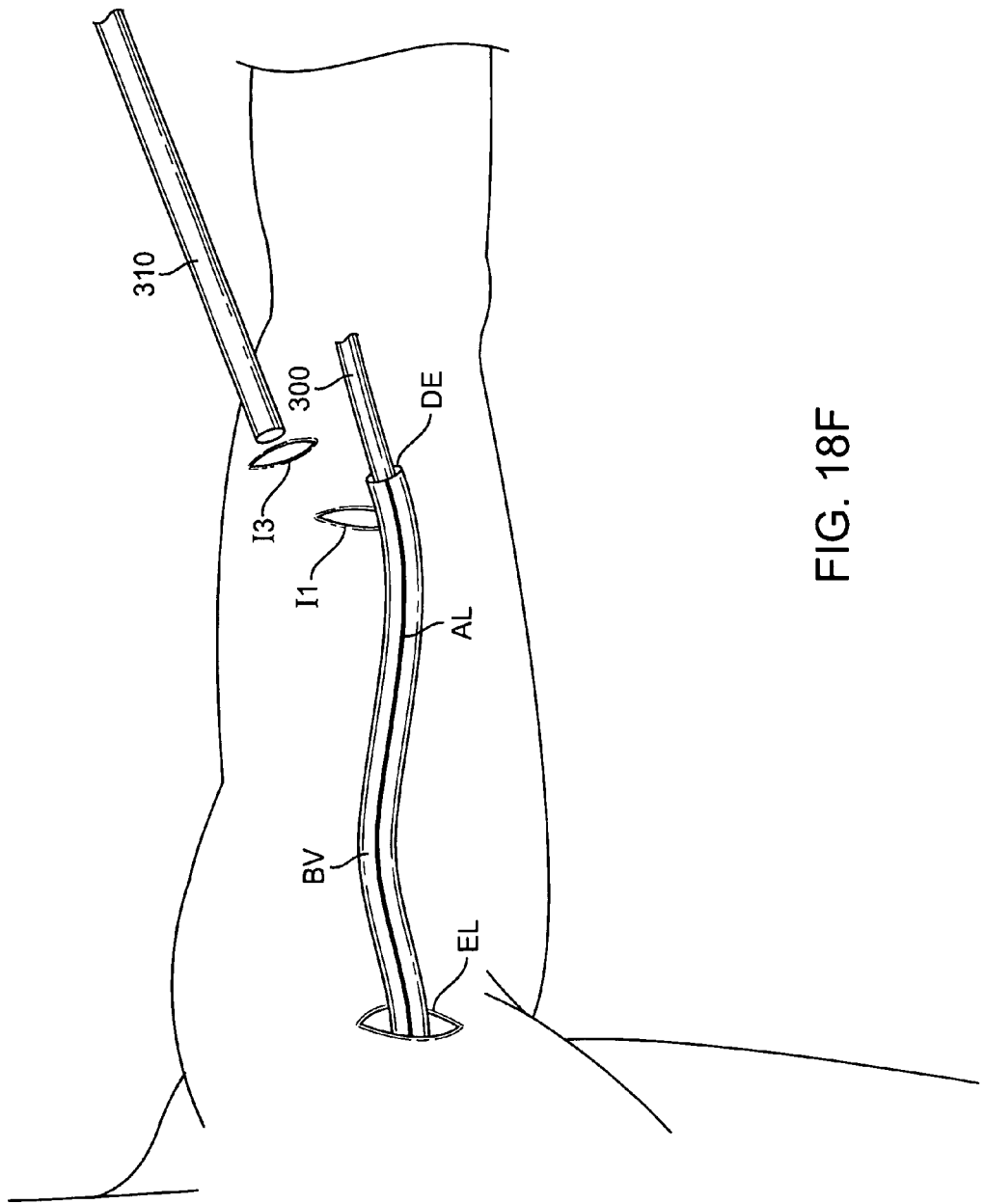
Figure 18G:
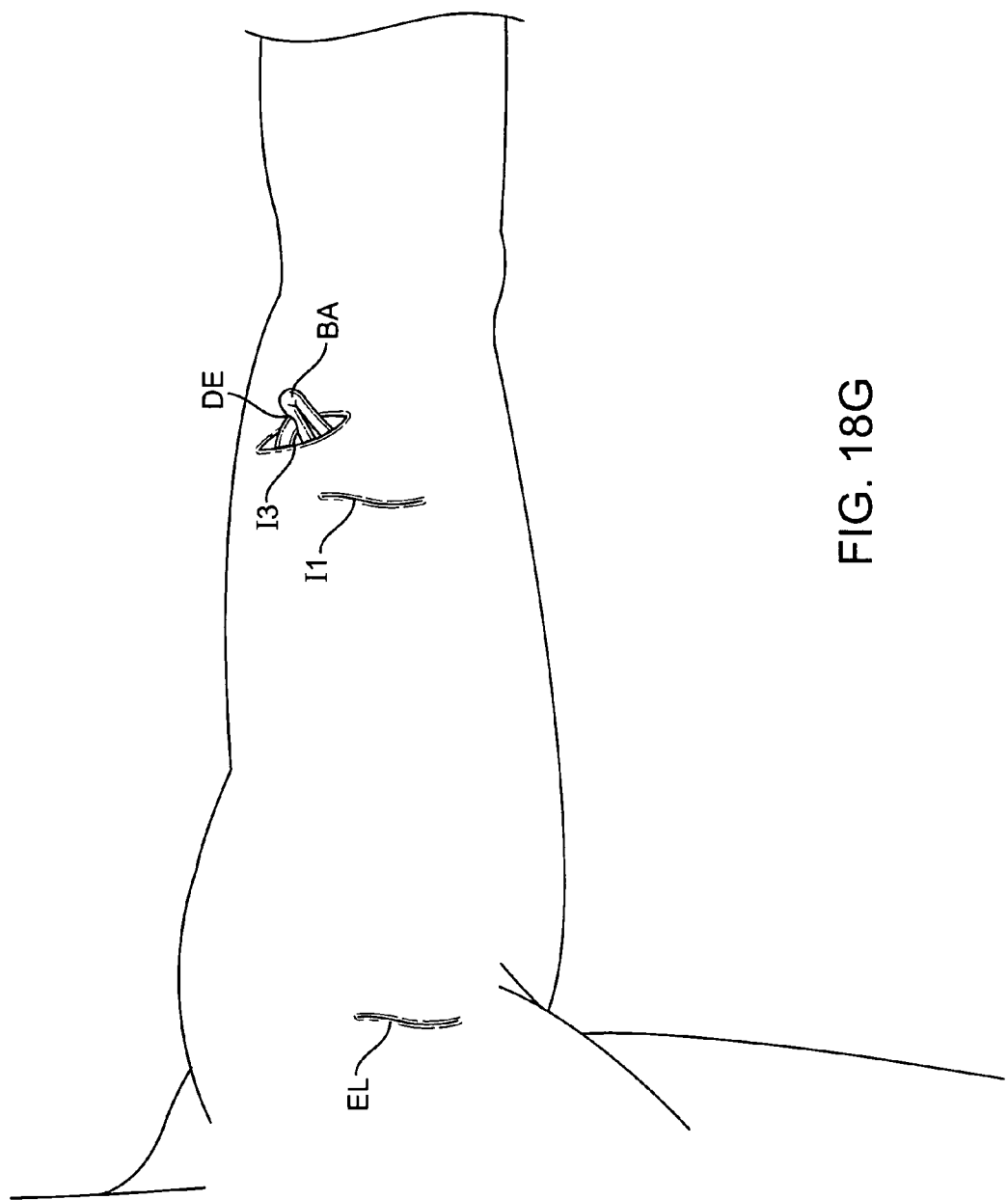

As shown in FIG. 18D, the catheter 300 is drawn out through the exposure location EL. As shown in FIG. 18E, the catheter 300 is then withdrawn distally to re-evert the basilic vein BV until it is fully externalized (FIG. 18F). A tunneling tool 310 is then introduced through a third incision I3 near the target site for attachment to the brachial artery BA (FIG. 18G). Tunneling tool 310 is advanced to the exposure location EL and used to draw the mobilized basilic vein BV back to the third incision I3. The vein is marked with an axial line AL to provide orientation and avoid twisting. After the vein BV is brought back to the third incision I3, the free distal end DE is anastomosed to the side of the brachial artery BA, as shown in FIG. 18G.

Further, while the invention has been shown and described with reference to an embodiment thereof, those skilled in the art will understand that the above and other changes in form and detail may be made without departing from the spirit and scope of the following claims.

What is claimed is:

1. A system for vein removal, said system comprising:
   a guidewire capable of extending from a proximal location to a space-apart distal location on a vein;
   a pull catheter adapted to be introduced over a proximal end of the guidewire in a distal direction and having means for attaching an excised end of the vein to a distal portion thereof so that the attached end can be pulled and inverted by the pull catheter; and
   side branch management tool adapted to be introduced over another end of the guidewire and having means for dissecting side venous side branches from the vein which are exposed as the vein is pulled in a proximal direction.

2. A system as in claim 1, wherein the guidewire has a length in the range from 180 cm to 260 cm and a diameter in the range from 0.2 mm to 0.9 mm.

3. A system as in claim 1, wherein the pull catheter comprises a catheter body having a length in the range from 40 cm to 80 cm.

4. A system as in claim 3, wherein the side branch management tool comprises a catheter body having a length in the range from 40 cm to 80 cm.

5. A system as in claim 1, wherein the attaching means on the pull catheter comprises an aperture or a circumferential trough for tying the vein thereto.

6. A system as in claim 1, wherein the pull catheter includes at least one lumen for receiving the guidewire.

7. A system as in claim 1, wherein the dissecting means on the side branch management tool comprises a blade.

8. A system as in claim 1, wherein the dissecting means comprises a blunt dissector.

9. A system as in claim 1, wherein the dissecting means comprises an electrosurgical tool.

10. A system as in claim 1, wherein the pull catheter further comprises a distal extension having a length generally equal to that of the catheter body.

11. A system as in claim 1, wherein the side branch management tool comprises means for selectively engaging and tensioning a side branch.

12. A system as in claim 11, wherein the tensioning means comprises a stop which is adapted to rotatorally engage and tension the side branch.

13. A kit for vein removal, said kit comprising:
    a guidewire;
    a pull catheter
    a side branch management tool; and
    instructions for use setting forth a method comprising:
       exposing first and second spaced-apart locations along a vein;
       transecting the vein at each location;
       passing the guidewire through a lumen of the vein between the first and the second location;
       introducing the pull catheter over the wire between the first location and the second location;
       attaching the vein to a distal end of the pull catheter at the second location;
       pulling the pull catheter from the second location to remove vein through the first location, wherein the vein is inverted with an inversion line which moves from the second location toward the first location as the vein is inverted; and
       excising venous side branches with the side branch management tool as the side branches are exposed by the inversion.

* * * * *